(12) United States Patent
Billinge et al.

(10) Patent No.: US 8,921,783 B2
(45) Date of Patent: Dec. 30, 2014

(54) METHOD OF COLLECTING AND PROCESSING ELECTRON DIFFRACTION DATA

(71) Applicant: The Trustees of Columbia University in the City of New York, New York, NY (US)

(72) Inventors: Simon Billinge, Brooklyn, NY (US); Christopher Farrow, Austin, TX (US); Tatiana E. Gorelik, Mainz (DE); Mercouri Kanatzidis, Wilmette, IL (US); Martin U. Schmidt, Frankfurt am Main (DE)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 14/160,185

(22) Filed: Jan. 21, 2014

(65) Prior Publication Data

US 2014/0306108 A1    Oct. 16, 2014

Related U.S. Application Data

(63) Continuation of application No. PCT/US2012/047568, filed on Jul. 20, 2012.

(60) Provisional application No. 61/510,280, filed on Jul. 21, 2011, provisional application No. 61/635,685, filed on Apr. 19, 2012.

(51) Int. Cl.
*H01J 37/26*    (2006.01)
*G01N 23/20*    (2006.01)

(52) U.S. Cl.
CPC .................................. *H01J 37/261* (2013.01)
USPC ........ 250/310; 250/307; 250/306; 250/492.3; 250/492.2; 438/487

(58) Field of Classification Search
CPC ................................................. G01N 23/20058
USPC .................. 250/310, 306, 307, 402.3, 492.2; 438/487

See application file for complete search history.

(56) References Cited

U.S. PATENT DOCUMENTS

| | | | |
|---|---|---|---|
| 5,080,495 A | 1/1992 | Hashimoto | |
| 5,644,391 A | 7/1997 | Grego | |
| 5,843,333 A | 12/1998 | Hakemi | |
| 6,267,864 B1 | 7/2001 | Yadav | |
| 6,570,163 B1 | 5/2003 | El Gomati | |
| 6,750,451 B2 | 6/2004 | Koguchi | |
| 6,989,542 B2 | 1/2006 | Moses | |
| 7,053,372 B2 | 5/2006 | Park | |
| 8,076,640 B2 * | 12/2011 | Koch | 250/307 |
| 8,253,099 B2 * | 8/2012 | Nicolopoulos et al. | 250/307 |
| 2003/0124077 A1 | 7/2003 | Pahlck | |
| 2004/0011958 A1 | 1/2004 | Wright | |
| 2007/0085003 A1 | 4/2007 | Miyazaki | |

(Continued)

FOREIGN PATENT DOCUMENTS

WO    WO-2010014512 A2    2/2010

*Primary Examiner* — Nikita Wells
(74) *Attorney, Agent, or Firm* — Lisa A. Chiarini; Walter M. Egbert, III; Hughes Hubbard & Reed LLP

(57) ABSTRACT

A method of using electron diffraction to obtain PDFs from crystalline, nanocrystalline, and amorphous inorganic, organic, and organometallic compound.

25 Claims, 21 Drawing Sheets

(56) References Cited

U.S. PATENT DOCUMENTS

| | | | |
|---|---|---|---|
| 2007/0243620 A1* | 10/2007 | Bates et al. ............... | 436/57 |
| 2008/0149831 A1 | 6/2008 | Saito | |
| 2009/0002708 A1 | 1/2009 | McFarland | |
| 2010/0000853 A1 | 1/2010 | Medoff | |
| 2010/0025579 A1 | 2/2010 | Bilhorn | |
| 2010/0108881 A1 | 5/2010 | Toth | |
| 2010/0108883 A1 | 5/2010 | Zewail | |
| 2011/0049363 A1 | 3/2011 | Koch | |
| 2011/0106455 A1 | 5/2011 | Billinge | |

\* cited by examiner

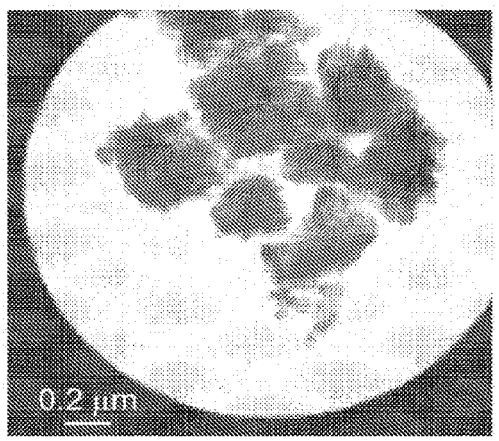
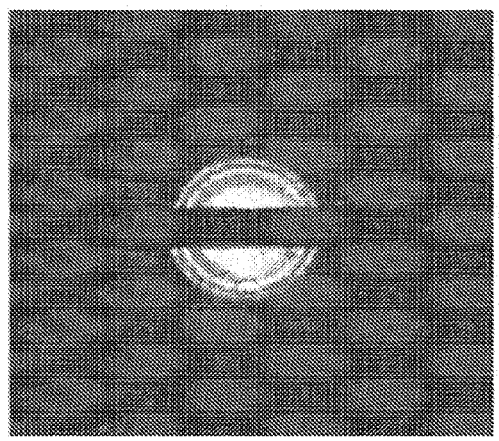
FIG.8A    FIG.8B
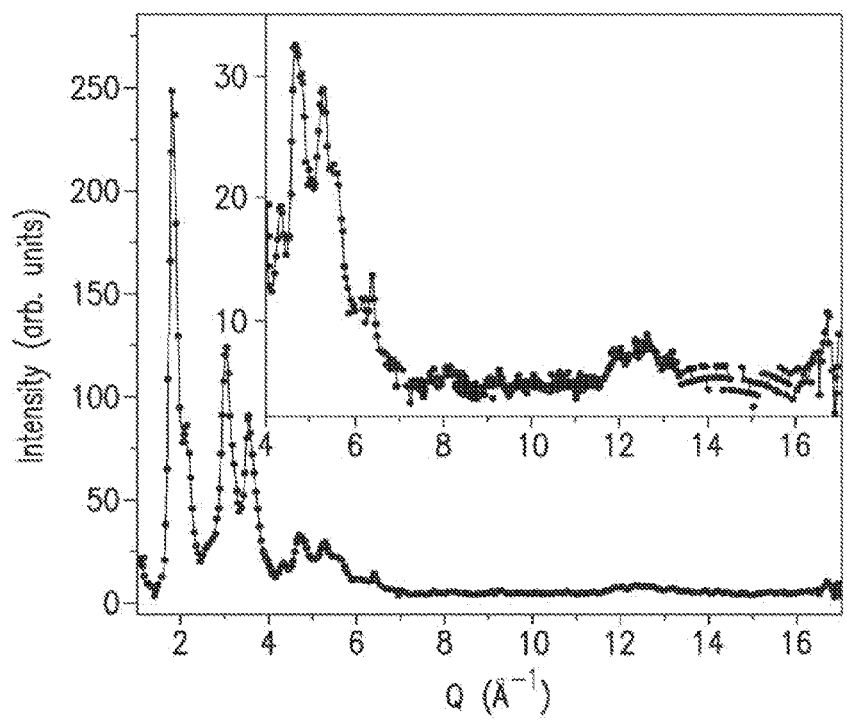
FIG.8C

QA

CuPc

CuPcCl

METHOD OF COLLECTING AND PROCESSING ELECTRON DIFFRACTION DATA

PRIORITY CLAIM

This application is a continuation of PCT/US2012/47568, filed Jul. 20, 2012 which claims priority to U.S. Provisional Application Ser. Nos. 61/510,280, filed Jul. 21, 2011 and 61/635,685, filed Apr. 19, 2012, the entire contents of each of which are incorporated herein in their entireties.

STATEMENT REGARDING FEDERALLY SPONSORED RESEARCH

This invention was made with government support under account DE-AC02-98CH10886 awarded by the Department of Energy Basic Energy Sciences and Grant No. DMR-07 awarded by the National Science Foundation. The government has certain rights in the invention.

FIELD

The subject matter relates, inter alia, to methods of collecting and processing electron diffraction data, including total scattering electron diffraction data.

BACKGROUND

Amorphous and nanocrystalline materials, including nanostructured bulk and nanoporous materials, have different properties than crystalline bulk materials. This is true for inorganic compounds, organic or organometallic materials, and metal-organic complexes. Examples include metallic nanoparticles and nanomaterials; organic pigments, where color may depend on crystallite size; organic semiconductors, where optical and electrical properties depend on crystallinity; and pharmaceutical compounds, where nanocrystalline and amorphous materials generally show increased solubility and bioavailability (Kim et al., 2008, Yu, 2001). Several active pharmaceutical ingredients (APIs) are industrially produced as nanocrystalline or amorphous powders (Prasad et al., 2010) through technologies such as cryomilling, melt extrusion, spray drying or rapid precipitation in the presence of crystallization inhibitors. Moreover, some APIs are produced and distributed in amorphous forms because they cannot be crystallized at all.

The properties of these amorphous or nanocrystalline materials depend strongly on their synthesis or processing conditions. A single "amorphous state" typically does not exist, but there can be substantial structural differences at the nanoscale for materials having an identical chemical composition but different processing history. Indeed, DSC, IR and Raman data reflect variations in analytical data of different "amorphous" batches of the same molecular system.

Despite the need for methods to characterize these materials, however, when the size, or range of structural coherence, of nanomaterials becomes small (e.g., less than 10 nm), traditional powder diffraction techniques, such as, e.g., the Rietveld method (Rietveld, 1969; Young, 1993), typically fail to yield reliable structural information (Billinge & Levin, 2007; Palosz et al., 2002). The atomic pair distribution function (PDF) analysis of x-ray and neutron powder diffraction data has shown itself to be a powerful method for nanostructures determination in this regime. Recently, the development of fast data collection strategies using 2D detectors, coupled with modeling improvements have allowed this approach to become broadly applied in many different chemical studies. During the last two decades, x-ray diffraction (XRD) and neutron diffraction (ND) have been the primary probes to obtain PDF data from structurally challenging materials.

PDF analysis has been a standard tool for the investigation of inorganic liquids and glasses for decades (Warren 1969, Klug & Alexander, 1974, Wagner 1978, Waseda, 1980, Wright 1985, Barnes et al., 2003). In recent years the PDF methodology was extensively applied to study nanostructured materials using short wavelength (epithermal) neutrons and high energy X-rays (Egami & Billinge, 2003; Billinge & Kanatzidis, 2004; Billinge 2008; Young & Goodwin, 2011). It was successfully applied to molecular compounds, including $C_{60}$ (Egami, and Billinge 2003), pharmaceutical materials (Billinge et al, 2010, Dykne et al. 2011), organic pigments (Schmidt, 2010), organometallic compounds (Petkov & Billinge, 2002) and metal-organic complexes (Wolf et al., 2012).

The powder diagrams for PDF analysis are usually recorded with neutron spallation sources or X-ray synchrotron sources. Generally, laboratory X-ray data can only yield sufficient quality PDFs for fingerprinting when a short-wavelength source (Mo or Ag anode) is used (e.g., see Dykne et al., 2011). Although this experimental setup can be realized in a laboratory, these instruments are very rare. Thus, the instrumental factors present a barrier to a broader application of the PDF method as a general characterization tool. A PDF experiment using electrons does not have this limitation: transmission electron microscopes (TEMs) are available at many labs. Furthermore, TEMs provide great flexibility when it comes to the measurement parameters. An operator can easily change the camera length thus setting various Q-ranges and electron wavelength if necessary. Furthermore, the operator can easily switch between imaging and diffraction mode, and can thus select from which area of the sample the diffraction pattern should be recorded. All these possibilities make PDF analysis from electron diffraction data an attractive alternative to X-rays or neutrons.

Electron diffraction (ED) has been long used for structure characterization of single nanocrystals (Dorset 1995). Due to the significant contribution of multiple scattering, ED was rarely used as an ab initio structure analysis technique, mainly supporting structure analysis based on a combination of other structural methods: X-ray powder diffraction (Gorelik et al., 2010), NMR (Lotsch et al., 2007), computational techniques (Voigt-Martin, 1995). Recently, with the development of 3D electron diffraction techniques, ab initio structure analysis of organic materials became possible (Kolb et al., 2010; Gorelik et al., 2012).

Powder electron diffraction (resulting in ring patterns) is usually used for structural fingerprinting (Làbàr, 2004; Moeck & Rouvimov, 2009). The intensity variations within the rings may also be used for texture analysis of nanocrystals (Gemmi et al., 2011), but usually the rings are azimuthally integrated into 1D diffraction profiles. Obtaining quantitatively reliable powder diffraction intensities from electron microscopes is very rare, with only a few examples of a quantitative structural analysis of powder electron diffraction data in the literature, all from inorganic compounds (Weirich et al., 2000, Kim et al., 2009, Luo et al., 2011). There are a number of reasons, including the strong tendency for electrons to diffract dynamically, the difficulty of obtaining good powder averages from such small volumes of material, and the propensity for the electron beam to damage the sample. Rietveld refinement of organic compounds from powder electron diffraction data has never been done so far.

A limitation of using electrons for quantitative structural studies can be that they interact with the material. Multiple scattering can be important in the resulting scattering which, in general, requires the use of dynamical scattering theory to be interpreted (Cowley, 2004) quantitatively and the simple kinematical scattering theory used in x-ray crystallography (Warren, 1990) and PDF analysis (Warren, 1990; Debye, 1915) may not be strictly valid. This can be circumvented when sample volumes are sufficiently small that multiple scattering events are not of high probability before the electrons exit the sample (e.g., typically a few nm of thickness), or when the scattering from the samples is highly incoherent, for example, the scattering from amorphous materials and away from zone axes in a crystal. In these latter cases there can be still significant multiple scattering, but it is typically sufficiently incoherent that it can be treated as a background and subtracted and the resulting coherent signal can be treated kinematically. This has been used in the rapidly growing field of electron crystallography, and has been demonstrated in previous work of electron diffraction from glasses (see, e.g., Moss et al., 1969; Hirotsu et al., 2003; Norenberg et al., 1999), although no quantitative modeling of the ePDF was attempted in those studies. In this respect, the study of small nanoparticles can be particularly favorable. The samples are typically thin, limited to the diameter of the nanoparticles which may be dispersed on a grid in a dilute way, and the structure is typically less coherent than from crystals because of the finite size effects that significantly broaden Bragg peaks and the often lower symmetries of nanoparticle structures due to surface and bulk relaxations. Fortuitously, the approximations are typically satisfied precisely for the small nanoparticles that can be most beneficially studied using PDF methods.

It is also possible that the interaction of the electron beam with a sample that is organic, organometallic, or a metalorganic complex, can damage the sample and alter the very structure that it is trying to measure. The methods described herein allow the intensity of the beam to be calibrated so that the resulting PDF remains reliable.

Exemplary embodiments of the present disclosure can provide methods, apparatuses, and computer-readable medium for obtaining quantitatively reliable PDFs from a normal transmission electron microscope (TEM) found in many research labs. For example, the resulting electron PDFs (ePDFs) can be modeled to extract quantitative structural information about the local structure using PDF refinements programs such as, e.g., PDFgui (Farrow et al., 2007). This can open the door to broader application of PDF methods for nanostructure characterization since TEM is typically already a routine part of the nanoparticle characterization process (Wang et al., 2000; Won et al., 2006), whereas x-ray PDF (xPDF) and neutron PDF (nPDF) studies typically require (or benefit from) access to intense synchrotron based x-ray and neutron sources. Accordingly, exemplary embodiments of the present disclosure can facilitate obtaining quantitative structural information, similar to that normally obtained from a Rietveld refinement in bulk materials, from nanoparticles with little additional effort. Embodiments of the present disclosure also can complement high resolution TEM by getting an average signal from a large number of nanoparticles rather than giving information from a small part of the sample that may not be representative.

The ability to obtain the real-space images and the diffraction data suitable for structural analysis at the same time and from the same region of material can be a large advantage, resulting in more complete information for the characterization of the sample. In some cases the small quantity of material required for ePDF, compared to xPDF and nPDF measurements, can also be a major advantage, as well as the ability to study thin films. In situations where the most information possible is required about a material, it can be desirable to carry out ePDF studies in conjunction with xPDF and nPDF studies, making use of the complementarity of these probes.

Exemplary embodiments of the present disclosure can be used/implemented/utilized to provide a collection of electron diffraction (ED) data resulting in quantitatively refinable ePDFs from several nanoparticle systems, which can be successfully modeled using standard PDF modeling software, demonstrating that exemplary embodiments of the present disclosure can be a viable and potentially powerful technique for nanoparticle studies.

Additional methods of analysis can also be found in U.S. patent application Ser Nos. 12/802,064, 13/310,683, 61/500, 787, 61/525,602, 61/563,258, and 61/510,280, the entire contents of which are hereby incorporated by reference.

SUMMARY

One aspect of the present disclosure is a method for determining an atomic pair distribution function of a sample using electron diffraction. According to this method, the sample is exposed to a beam of electrons. The sample causes electrons to scatter from the beam, the scattered electrons are detected, and a diffraction pattern of the sample is produced. Either the sample or the electron beam can be manipulated to limit the exposure of the sample to the electron beam. Limiting the sample's exposure to the electron beam can reduce damage to the sample. Finally, the signal is analyzed to determine the atomic pair distribution function of the sample.

In one embodiment of the current aspect, the sample may be a thin film. In another embodiment, the exposure of any one portion of the sample material is kept below the critical electron dose. For example, the critical electron dose may be the electron dose that causes less than 37% (about 1/e) decay of the Bragg intensities. In another embodiment the electron dose is kept below a value that causes less than 5% decay of the Bragg intensities. Alternatively the critical electron dose may be the electron dose that causes less than 37% change of the height of a peak in the PDF that is not a near-neighbor peak. In another embodiment the electron dose is kept below a value that causes less than 5% change of the height of a peak in the PDF that is not a near-neighbor peak. Alternatively, the critical electron dose may be the electron dose that causes less than a 5% change in the height of a peak in the PDF that is not a near-neighbor peak. In another embodiment, the signal may be obtained by a low-voltage electron microscope. The electron microscope may operate, for example, at a voltage lower than 80 kV, lower than 50 kV, lower than 10 kV, or lower than 5 kV. In another embodiment, the signal may be obtained, for example, by a transmission electron microscope that is equipped with an STEM unit. In a further embodiment, the diffraction pattern is recorded as a two-dimensional image. In further embodiments, the electron beam may pass through the sample and may impact a corner of the detector or the center of the detector, or may not impact the detector. The diffraction pattern may be obtained in either transmission or reflection geometry.

In another embodiment, the method may include analysis of the image by appropriately normalized azimuthal integration. According to this embodiment, the diffraction pattern is recorded as a two-dimensional image, and the location of the central beam is recorded. The image is then azimuthally integrated about the central beam location to obtain the integrated intensity as a function of an independent variable x, which may represent Q, S, 2θ, or any other useful independent variable known to those of ordinary skill in the art. The background intensity may also be azimuthally integrated to obtain the background as a function of the independent variable, and the background intensity may then be subtracted from the integrated intensity. It is also possible, and sometimes desirable, to perform the background subtraction on the raw images before the azimuthal integration step. Once the intensity is obtained as a function of x, it is corrected for intensity aberrations to obtain i(x), which may optionally be further normalized to obtain F(x), which may in turn may be Fourier transformed to obtain the pair distribution function.

In another embodiment, the sample is an organic material and may be, for example, an active pharmaceutical ingredient, an organic pigment, an organic dyestuff, an organic polymeric material, an organic semiconductor, or an organic liquid crystal. In another embodiment, the sample is an organometallic material and may be, for example, an active pharmaceutical ingredient or a catalyst. In another embodiment, the sample is a metal-organic complex and may be, for example, a laked pigment, a metal-containing organic dyestuff, or a polymeric metal-organic material.

In another aspect, the present disclosure describes a method for collecting electron diffraction data from one or more substantially unexposed areas of an organic or organometallic sample. The organic or organometallic sample includes pharmaceutical compositions and/or active pharmaceutical ingredients. In this method, the sample is illuminated with an electron beam that has diameter $D_0$ where it intersects the sample, and electron diffraction data is collected from the sample. This procedure may then be repeated on other areas of the sample.

In one embodiment, a selected area aperture with diameter $D_{SA}$ may be inserted between the sample and the detector. $D_0$ may be greater than $D_{SA}$. In a further aspect of this embodiment, $D_0$ or $D_{SA}$ may be selected according to the size of physical or chemical features in the sample. For example, $D_{SA}$ may be selected so that a signal is collected from only one region of the sample. In another embodiment, the electron beam may be either parallel or focused. In another embodiment, a condenser aperture may be inserted between the electron source and the sample. In another embodiment, $D_0$ may be as small as a few nanometers. More specifically, $D_0$ may be 10 nm, 5 nm, 2 nm, or 1 nm.

In another aspect, the present disclosure describes a method for determining one or more atomic pair distribution functions associated with an organic or organometallic material. In one embodiment of this aspect, several regions of a sample are identified. An electron diffraction signal is obtained from each region, and the signal from each region is classified. The number of distinct structural forms that have been identified is determined, and the PDF associated with each of the distinct structural forms also determined.

In one embodiment of this aspect, the regions are identified after a visual inspection of an electron microscope image of the sample. In another embodiment, the regions are identified based on a visual inspection of the diffraction pattern. In another aspect of this embodiment, the signals may be classified based on a visual inspection of an electron microscope image of the sample. In another embodiment, the signal may comprise an image. In another embodiment, the signals may be classified based on a visual inspection of a diffraction pattern. In another embodiment, the number and identity of structural types identified may be determined by examining the entire set of diffraction patterns as a whole. In yet another embodiment, the signals obtained may be classified according to whether the diffraction pattern arises from the sample, or from a substrate. Alternatively, when the sample is supported on a holey carbon grid with a copper mesh, the signals may be classified according to whether the diffraction pattern arises in whole or in part from the material, the carbon film, or the copper grid. In another embodiment, the sample may be supported on a carbon film or a polymeric film.

In another aspect, the present disclosure is a method for determining an atomic pair distribution function of a sample using electron diffraction. According to this method, the sample is exposed to a beam of electrons. The sample causes electrons to scatter from the beam, the scattered electrons are detected, and a diffraction pattern of the sample is produced. Finally, the signal is analyzed to determine the atomic pair distribution function of the sample.

In one embodiment of the current aspect, the sample may be a thin film or may have a thickness that is sized to reduce scattering of the electrons. In another embodiment, the signal may be obtained by a low-voltage electron microscope. The electron microscope may operate, for example, at a voltage lower than 80 kV, lower than 50 kV, lower than 10 kV, or lower than 5 kV. In another embodiment, the signal may be obtained, for example, by a transmission electron microscope that is equipped with an STEM unit. In a further embodiment, the diffraction pattern is recorded as a two-dimensional image. In further embodiments, the electron beam may pass through the sample and may impact a corner of the detector or the center of the detector, or may not impact the detector. The diffraction pattern may be obtained in either transmission or reflection geometry.

In another embodiment, the method may include analysis of the image by appropriately normalized azimuthal integration. According to this embodiment, the diffraction pattern is recorded as a two-dimensional image, and the location of the central beam is recorded. The image is then azimuthally integrated about the central beam location to obtain the integrated intensity as a function of an independent variable x, which may represent Q, S, 2θ, or any other useful independent variable known to those of ordinary skill in the art. The background intensity may also be azimuthally integrated to obtain the background as a function of the independent variable, and the background intensity may then be subtracted from the integrated intensity. It is also possible, and sometimes desirable, to perform the background subtraction on the raw images before the azimuthal integration step. Once the intensity is obtained as a function of x, it is corrected for intensity aberrations to obtain i(x), which may optionally be further normalized to obtain F(x), which may in turn may be Fourier transformed to obtain the pair distribution function. In one embodiment of this aspect, the sample may be sized to reduce scattering of electrons.

In another aspect, the present disclosure describes a non-transitory computer-accessible medium that includes instructions for generating an atomic pair distribution function of a sample according to the methods disclosed herein. In one embodiment of this aspect, the sample may be sized to reduce scattering of electrons.

In another aspect, the present disclosure describes a system for generating an atomic pair distribution function of a sample according to the methods herein. The system includes a non-transitory computer-accessible medium that contains instructions for generating an atomic pair distribution function of a sample according to the methods disclosed herein. In one embodiment of this aspect, the sample may be sized to reduce scattering of electrons.

BRIEF DESCRIPTION OF THE DRAWINGS

FIGS. 8A-C depict TEM and ED data for HgS nanoparticles.

DETAILED DESCRIPTION

Structural characterization of inorganic amorphous materials can be performed using the pair-distribution function (PDF). The PDF G(r) represents the probability to find a pair of atoms with an interatomic distance r, weighted by the scattering power of the individual atoms. Such an approach is equally applicable to amorphous and nanostructured organic materials, as recently demonstrated (Bates et al., 2006, Billinge et al. 2010, Dykne et al. 2011) where for a molecular crystal, the PDF profiles include intramolecular distances as well as the interatomic distances between different molecules.

The PDF can be obtained from powder diffraction data after proper normalization and corrections to obtain the reduced scattering function F(Q) (Warren 1969, Egami & Billinge 2003, Farrow & Billinge 2009)

$$G(r) = \frac{2}{\pi} \int_{Q_{min}}^{Q_{max}} Q[F(Q) - 1] \sin(Qr) dQ$$

where Q is the magnitude of the scattering vector. For elastic scattering, $$Q = \frac{4\pi \sin\theta}{\lambda}$$

The PDF can also be related to the atomic structure through, e.g.:

$$G(r) = \frac{1}{r} \sum_{i,j} \frac{f_i(0) f_j(0)}{\langle f(0) \rangle^2} \delta(r - r_{ij}) - 4\pi r \rho_0$$

Here the sum runs over the pairs of atoms i and j, which are separated by r in the model. The scattering factor, or form factor, of atom i is $f_i(Q)$ and $\langle f(Q) \rangle$ is the scattering amplitude averaged over the atoms in the sample. In the exemplary equation above, the scattering factors are evaluated at Q=0, which in the case of x-rays can be the atomic number of the atom. The double sum is taken over all of the atoms in the sample. For a multicomponent system, S(Q) can be written in terms of the concentrations, $c_i$, of the atoms.

$$S(Q) = 1 + \frac{I(Q) - \Sigma c_i |f_i(Q)|^2}{|\Sigma c_i f_i(Q)|^2}$$

Figure 1:
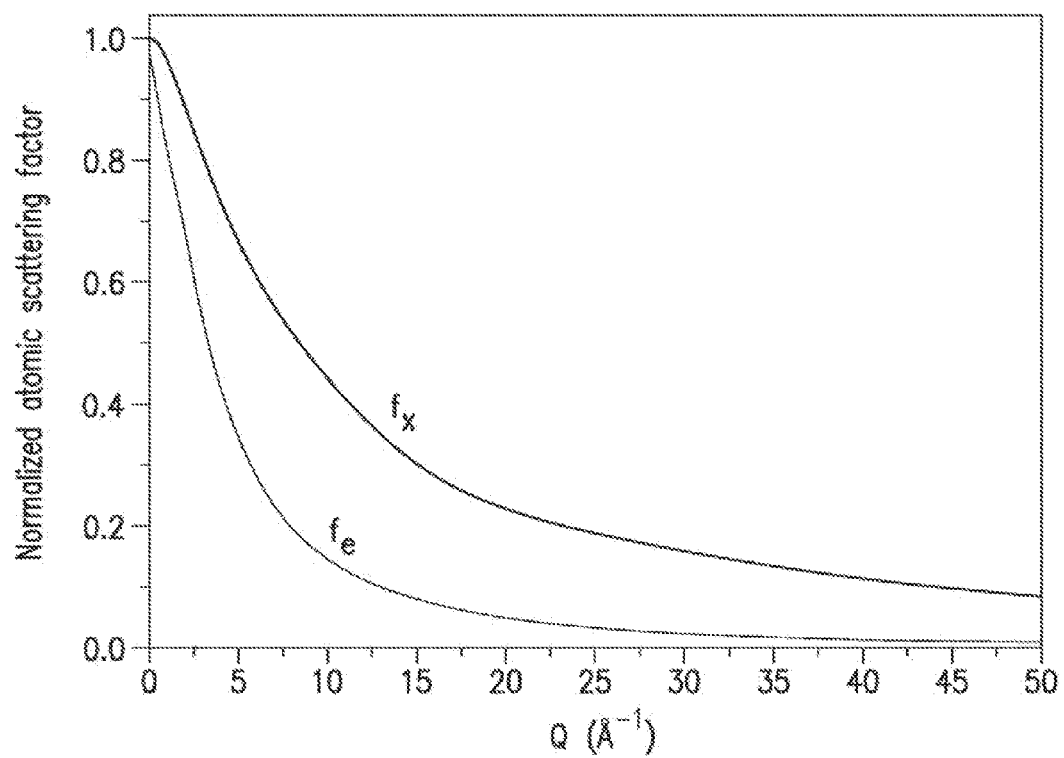
FIG. 1 depicts a comparison between normalized x-ray and electron form factors.

In the case of electrons as a probe the equations are the same, providing the scattering can be treated kinematically, but the form-factor must be that appropriate for electrons, $f_e(s)$, which is the Fourier transform of the electronic potential distribution of an atom. In the electron literature, it is conventional to use s=sin θ/λ instead of Q for the dependent variable in the scattering. The electron form factor, $f_e(s)$, is different from, but is still related to, the x-ray form factor of the same atom, $f_x(s)$, which is be the Fourier transform of the electron density. A useful relationship between $f_e(s)$ and $f_x(s)$ is:

$$f_e(s) = \frac{m_e e^2}{2h^2} \left( \frac{Z - f_x(s)}{s^2} \right)$$

where $m_e$ and e are the mass and charge of the electron, respectively, h is Planck's constant, and Z is the atomic number. This exemplary equation may not give a definite value for $f_e(s)$ at s=0, but $f_s(0)$ can be calculated by extrapolation or by using, e.g.:

$$f_e(0) = 4\pi^2 \frac{me^2}{3h^2} (Z\langle r^2 \rangle)$$

where $\langle r^2 \rangle$ is the mean square radius of the electronic shell of the atom. FIG. 1 shows, for example, a comparison between x-ray and electron form factors, $f_x(s)$ and $f_e(s)$, of Au.

In the case of single crystal ED, when the crystal thickness is greater than, for example ~300-400 Å, data reduction is preferably done based on the dynamical diffraction theory, which can handle the presence of coherent multiple scattering components of electrons. Depending on the energy of the electrons, this thickness limit may fall below the above numbers in the presence of heavy elements, and in the case of electron powder diffraction, the average thickness of crystallites in the specimen is preferably also be less than a few hundred Angstroms to avoid dynamical scattering effects.

(Cowley, 1995). Coherent multiple scattering can change the relative intensities of Bragg peaks from the kinematical structure factor values, and can facilitate symmetry disallowed peaks to appear in the pattern. Incoherent multiple scattering can be observed in ED patterns in the form of increased background, but does not affect the relative intensities of the Bragg peaks. Accordingly, in the case of a less coherent structure, dynamical scattering effects are typically less important.

In exemplary implementations and/or experiments utilizing exemplary embodiments of the present disclosure, the specimens were, for example, nanosized samples, e.g.: thin films, discrete nanoparticles, and/or ball milled agglomerates with very short structural coherence lengths. The samples can have a correlation length in the range 20-40 Å. In these exemplary cases, multiple scattering did introduce undue aberrations into the kinematical diffraction pattern and reliable PDFs resulted.

Exemplary Data Collection and Analysis Procedure for Non-Beam-Sensitive Samples

Figure 2A:
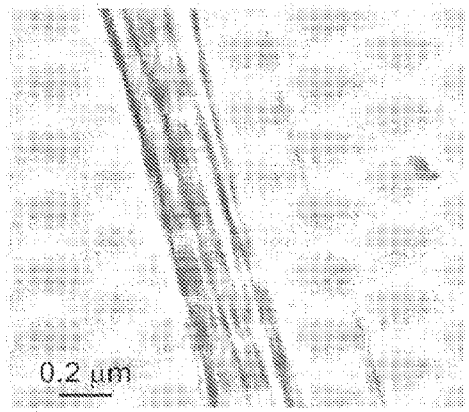
FIGS. 2A-C depict TEM and ED data for a 2.7 nm Au film.
Figure 2B:
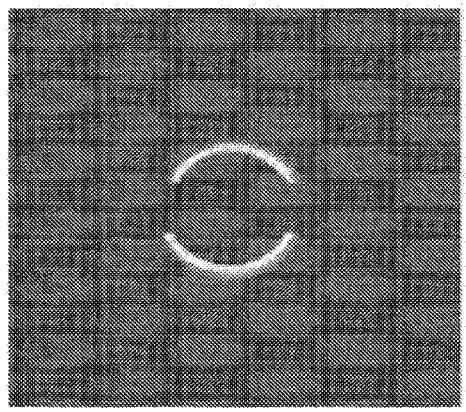

A low resolution TEM image of a 2.7 nm thick Au film is shown in FIG. 2(a). The film is uniform and featureless in the image, but a region at the edge of the film was selected so that the edge of the film gives a visual cue. An ED pattern from a similar region of the sample is shown in FIG. 2(b). A series of concentric circles due to the Scherrer powder diffraction rings in transmission geometry can be seen. The 2D ED image was read and integrated into a 1D powder diffraction pattern in FIG. 2(c) using the software package Fit2D29, after masking the missing beam stop region.

The ED pattern from a standard of known lattice parameter may be used to calibrate the conversion from detector coordinates to scattering angle. The analysis software can use this to optimize the effective sample-detector distance, find the center of the Scherrer rings on the detector, and correct for aberrations such as any deviation from orthogonality of the detector and the scattered beam. Typical standards used by the program can be $Al_2O_3$, $CeO_2$, $LaB_6$, NaCl and Si. However, for the exemplary electron diffraction experiment it can be preferable to have a nanosample to obtain a good powder average. Accordingly, gold nanoparticles of diameter ~100 nm can be used, and a literature value of 4.0782 Å for the lattice parameter can be used. In general, sample-detector distance can depend on the settings of the magnetic lenses used in the microscope. The energy of the electrons, e.g., 200 keV, is well known (e.g., resulting in $\lambda=0.025079$ Å), though for the most accurate results, the electron wavelength can be preferably calibrated using standard methods. Once these calibration quantities are known, they can be fixed and the values can be used to convert the sample data. From this perspective, it can be preferable that the sample is measured under identical conditions as the standard, including camera length and focus. Scanning around a sample to find a different viewing area can result in a small variation in the position on the detector of the center of the resulting diffraction pattern. It can be thus preferable to run a separate calibration run on each diffraction pattern to determine the center of the rings, while keeping the camera-length from the Au calibration.

Figure 2C:
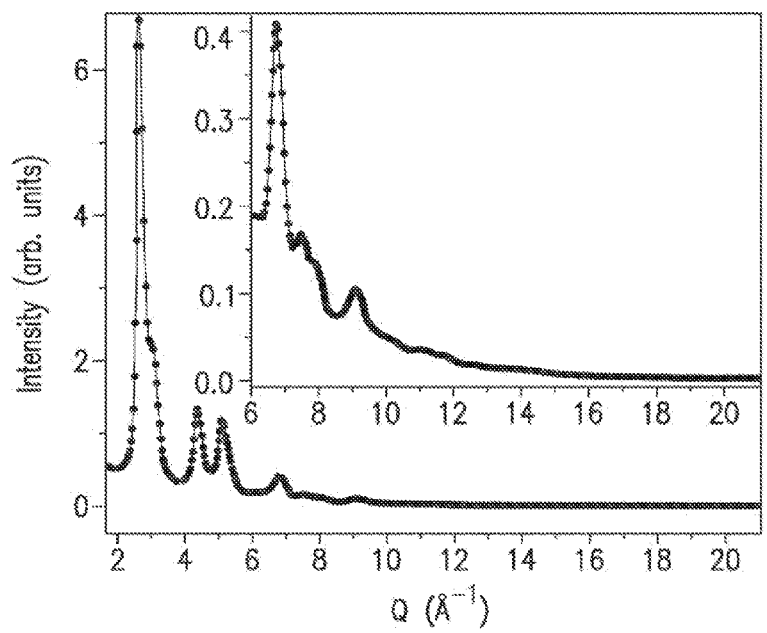
Figure 3A:
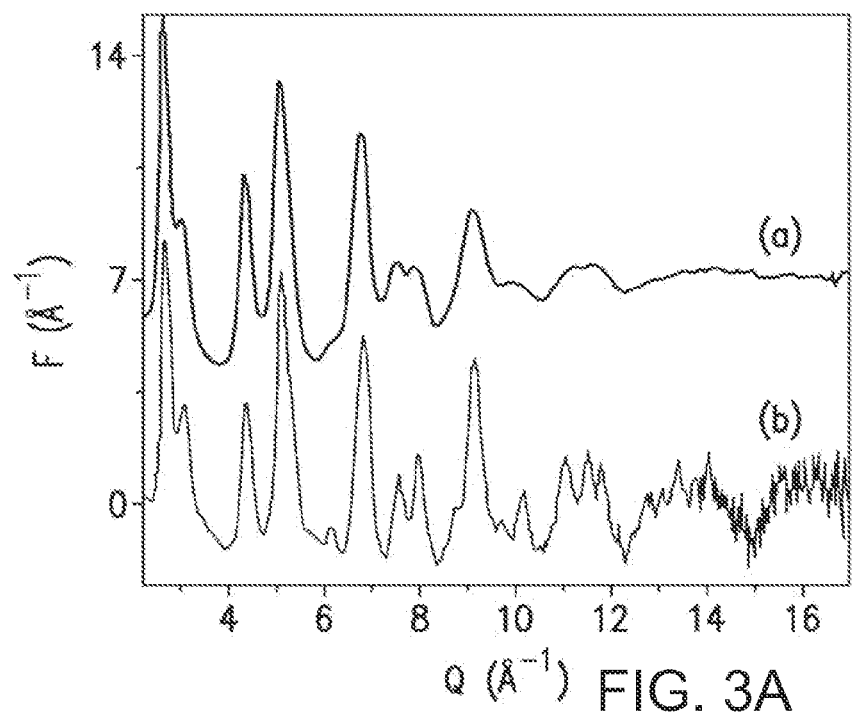
FIGS. 3A & 3B depict RSFs and PDFs of an Au film, measured with both electron and x-ray diffraction.

An exemplary 1D ED pattern, obtained by integrating around the rings in the 2D pattern shown in FIG. 2(b), is shown in FIG. 2(c). The data can be further processed to obtain the PDF. Corrections can be applied to the raw data to account for experimental effects (Egami & Billinge, 2003), and the data can be normalized and divided by $\langle f_e(Q)\rangle^2$, resulting in the total scattering structure function, S(Q). The kernel of the Fourier transform can be, for example, the reduced structure function, $F(Q)=Q[S(Q)-1]$. A program (e.g., PDFgetE) can be used to carry out these steps, resulting in the F(Q) for the gold nanoparticles shown in FIG. 3(a). The PDF can then be straightforwardly obtained as the Fourier transform of F(Q) according to, for example, Eq. 1. This step may also be carried out using a program such as PDFgetE. The resulting ePDFs of the gold nanoparticles are shown in FIG. 3(c).

Once the exemplary ePDFs are obtained, they can be modeled, for example, using existing PDF modeling programs. Here, PDFgui (Farrow and Juhas, 2007) can be used. The structure model used in this example was the fcc bulk gold structure. The refined variables may include cubic lattice parameters and isotropic atomic displacement parameters as well as a term to account for the fall-off in PDF peak intensity due to the finite resolution of the ED measurement.

The exemplary results obtained from the ED data of gold and NaCl can be compared to similar results from x-ray derived PDFs (xPDFs) collected using standard methods (Chupas et al., 2007) at an x-ray synchrotron source. In this exemplary case, beamline, X7B at the National Synchrotron Light Source (NSLS) at Brookhaven National Laboratory (BNL) was used. Data processing has been described in detail elsewhere (Egami & Billinge 2003). 2D imageplate images are integrated, for example, using Fit2D (Hammersley, 1998) to obtain the 1D powder pattern. These can be further processed using, for example, PDFgetX2 (Qiu et al., 2004) to obtain F(Q) and the x-ray G(r). For comparison, the PDFs were calculated using the same Qmax value as the ePDFs, with Qmax=15.25 and 13.6 Å$^{-1}$ for the Au and NaCl cases, respectively. The xPDFs were fit using the same models as the ePDFs using PDFgui (Farrow et al., 2007).

Exemplary Data Collection and Analysis Procedure for Beam-Sensitive Materials

The present disclosure also provides methods for the collection of powder electron diffraction data from beam sensitive materials and the specific points of data processing and generating PDFs for these compounds.

Figure 10C:
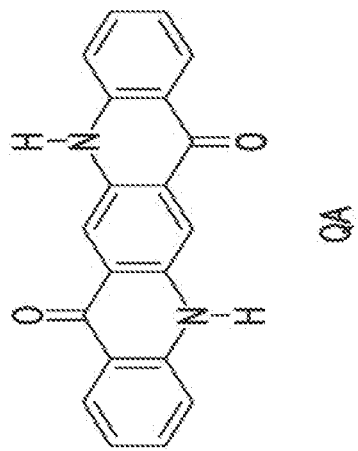
FIGS. 10A-10C depict the chemical structures of (a) chlorinated copper-phthalocyanine (CuPcCl), (b) copper-phthalocyanine (CuPc) and (c) quinacridone (QA).
Figure 10B:
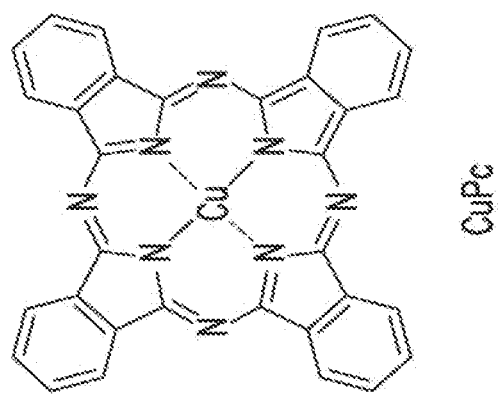
Figure 10A:
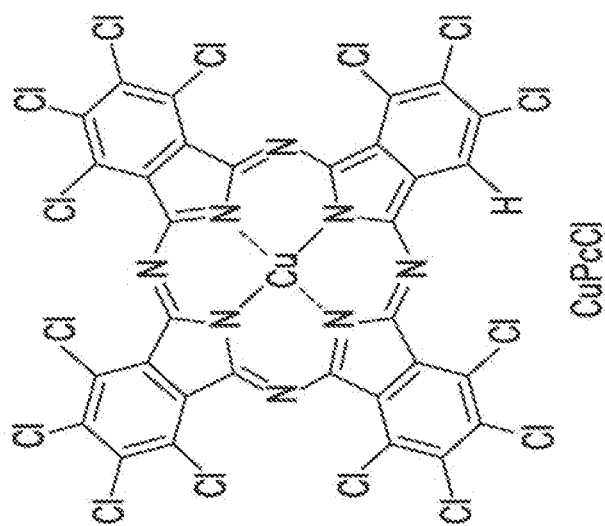

FIG. 10 depicts three representative organic compounds: (a) chlorinated copper-phthalocyanine (CuPcCl), (b) copper-phthalocyanine (CuPc) and (c) quinacridone (QA). CuPcCl is a mixture of isomers and molecules with different degree of chlorination, with about 15 Cl atoms on average.

The first compound, CuPcCl, is commonly used as a reference material in HRTEM imaging. The compound has the chemical composition $CuC_{32}N_8Cl_xH_{16-x}$ with x equal to about 15, and is registered in the International Colour Index as C.I. Pigment Green 7. An advantage of this material is that it is not beam-sensitive. The second compound, an example of a beam-sensitive material, CuPc has the chemical composition CuC32N8H16 and was used in its β-modification (C.I. Pigment Blue 15:3). The third compound, QA, is a purely organic compound with chemical composition $C_{20}H_{12}N_2O_2$ that is also beam-sensitive. It was used in its γ-modification (C.I. Pigment Violet 19).

CuPcCl is a deep green shade, β-CuPc is a standard blue, and γ-QA exhibits a bluish red shade. All three compounds are industrially produced on large scale and used as pigments for coloring lacquers, coatings, plastics, printing inks, and artists' colors. The compounds are also organic semiconductors which can be used in optoelectronic devices such as organic LEDs or photovoltaic systems. The crystal structures of β-CuPc and γ-QA are known from X-ray single-crystal structure analyses.

Electron diffraction data on these compounds was collected with a TECNAI F30 transmission electron microscope equipped with a field-emission gun operating at 300 kV and a STEM unit. The diffraction data were recorded on a 1 k GATAN CCD camera. Diffraction patterns were collected with a camera length of 380 mm. In order to increase the Q-range of the data, the central (transmitted) beam was kept at a corner of the CCD area. In alternative embodiments, electron diffraction data may be collected by any appropriate method known to one of ordinary skill in the art. For example, electron diffraction data may be collected on a standard transmission electron microscope, on a low-voltage electron microscope, or on a scanning electron microscope equipped with a STEM unit.

Inelastic scattering from collisions between electrons and the material being studied deposits energy into the material, which is then released by different means—either transformed into thermal vibration of the molecules, or into excitation of individual molecules which eventually can cause ionization and reorganization of molecular structure (e.g., bond cleavage and formation of cross-linked aggregates). Typically in electron crystallography beam damage is observed as loss of crystallinity of the material as a result of electron irradiation. As beam damage can cause reorganization of the molecular structure, it is a serious concern also for poorly crystalline and amorphous organic materials. In one embodiment of the present disclosure, beam damage is reduced to allow for quantitative determination of the PDFs of undamaged materials.

Collective beam damage effects may be quantified using the deterioration of the crystalline lattice, which is only possible for materials showing distinct Bragg peaks in diffraction patterns. It is unclear if the estimates of the critical electron dose for crystalline materials can be directly transferred to the amorphous state. The PDF analysis, being sensitive to the local structure and molecular packing should be the ultimate tool to study the collective radiation damage effects in organic materials.

There are several methods to improve the stability of organic material under electron radiation—cooling, enhancing the charge and heat transfer, but the most fundamental solution is a significant decrease of the intensity of the incident electron beam. The counteracting consideration to decreasing the illumination level is the need to obtain reasonable counting statistics on the detector. Contemporarily most of the TEM work is recorded onto CCD cameras or image plates. Recently, detectors built on CMOS technology for TEM appeared on the market having superior sensitivity and therefore high potential for low-illumination level TEM investigations including diffraction data acquisition for beam-sensitive materials. The present disclosure therefore describes a method for reducing damage to an organic or organometallic material by limiting the exposure of the material to the electron beam.

In the present disclosure, three poorly crystalline organic samples were used. Diffraction patterns of all these materials showed sharp Bragg-like peaks indicating that they have some crystallinity and are not truly amorphous.

As an initial check for beam damage a series of diffraction patterns were collected from the same position on the samples showing a continuous decay of the reflection intensities. From the intensity decay plots a critical electron dose was estimated. During the diffraction data collection for the PDF analysis electron dose rates were used causing less that 5% decay of the Bragg intensities (exact values are given below separately for each experimental setup). Setting up the illumination conditions much below the critical electron dose is essential for ensuring the resulting PDFs are a good measure of the original structure of the materials under study.

Selected Area Electron Diffraction (SAED) vs. Nanodiffraction

In one embodiment of the present disclosure, selected area electron diffraction (SAED), the sample is illuminated with the parallel beam having a certain diameter $D_0$. A selected area aperture with an effective diameter at the sample of $D_{SA}$ is inserted between the specimen and the detector. In order to keep the incident beam parallel and to have well defined diffraction geometry $D_0$ is usually kept large, while $D_{SA}$ is selected according to the size of the specimen features (for instance, crystal size). In this geometry, the illuminated sample area, which is the area subject to eventual beam damage is large, while the area effectively used for diffraction data collection, $D_{SA}$, is just a small fraction of it. Nevertheless, when the $D_0$ is known a new diffraction pattern can be collected from fresh (unexposed area) using a stage shift of greater than $D_0$. This classical SAED geometry can be used when diffraction lens settings cannot be changed and the sample features are relatively small.

For beam sensitive materials the SAED geometry may be modified by focusing the incident beam to reduce the diameter of the illuminated area $D_0$. In a preferred embodiment, the selected area for the diffraction information is collected from the same area that is illuminated ($D_0=D_{SA}$). For these conditions there is no need to use the selected area aperture. Combining different condenser lens settings and condenser aperture size one can obtain any beam size at the specimen in principle down to a few nanometers; therefore this diffraction geometry is called nanodiffraction. However, it must be noted that, to collect diffraction patterns of poorly crystalline materials with good statistics and a reasonable powder average, the actual area may be hundreds of nanometers or more.

Figure 11A:
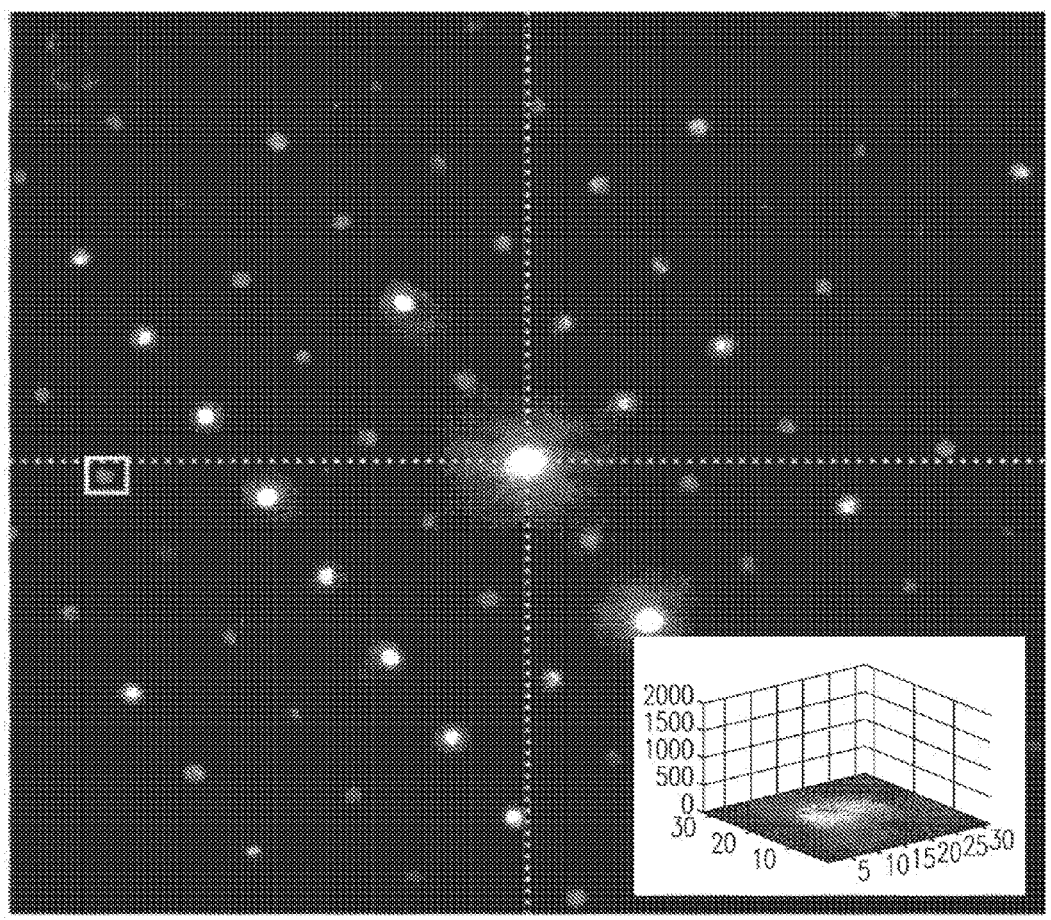
FIGS. 11A-11C depict nanodiffraction patterns of $MoO_3$ and a plot indicating the diffraction lens current according to effective camera length.
Figure 11B:
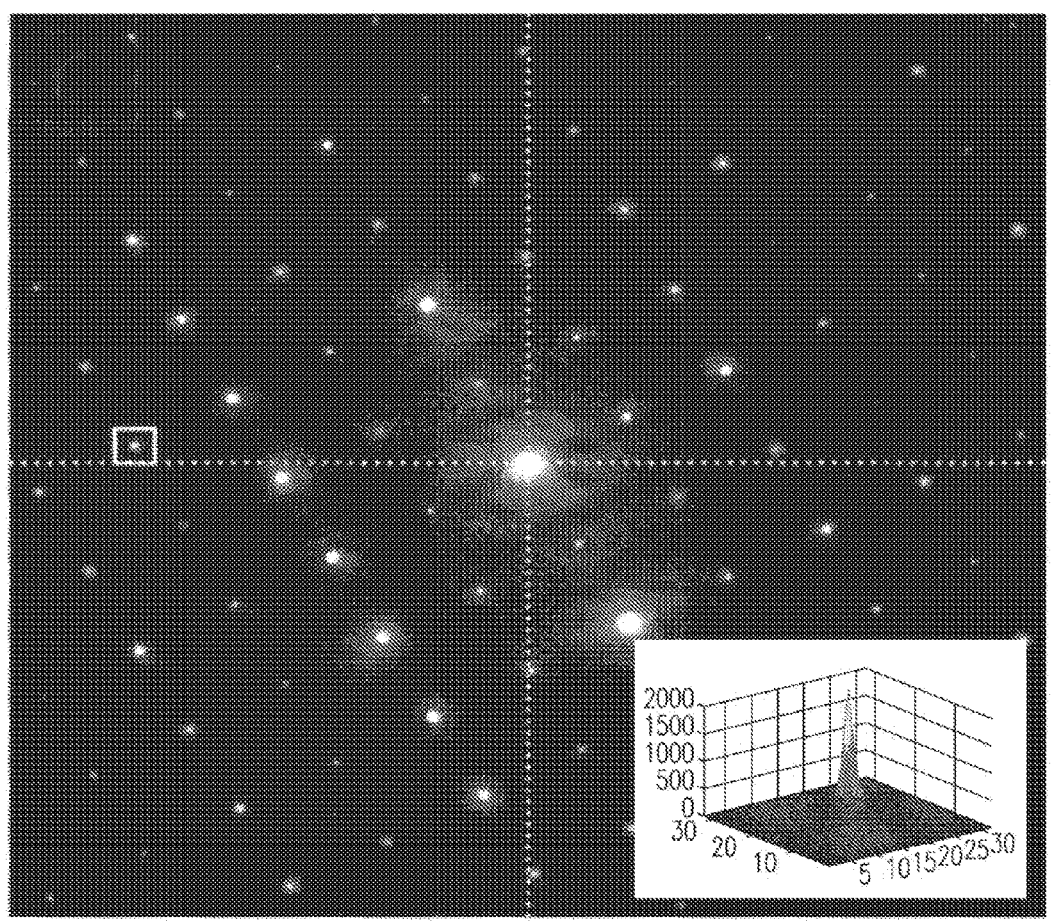

A key step in the analysis of a diffraction pattern is to convert the diffraction image from detector units to Q or some other appropriate independent variable known to one of ordinary skill in the art. To do this the electron wavelength and effective camera length must be known. FIG. 11 depicts one method to carry out this conversion. Typically the electron diffraction camera length is calibrated using a known standard material at specified illumination conditions (state of the condenser lens current). In FIG. 11, the standard material is $MoO_3$. For these illumination conditions the diffraction pattern is focused using the diffraction lens. Selecting the illuminated area for nanodiffraction implies free modification of the illumination conditions and thus the convergence of the beam. As a result, the corresponding diffraction pattern in FIG. 11(a) is acquired at non-standard lens settings, and appears defocused. Additional focusing of the diffraction pattern causes rotation and contraction/expansion of the diffraction pattern, as depicted in FIG. 11(b). The rotation is not relevant for powder (ring) patterns, but the contraction/expansion changes the effective camera length and therefore has to be taken into account.

Figure 11C:
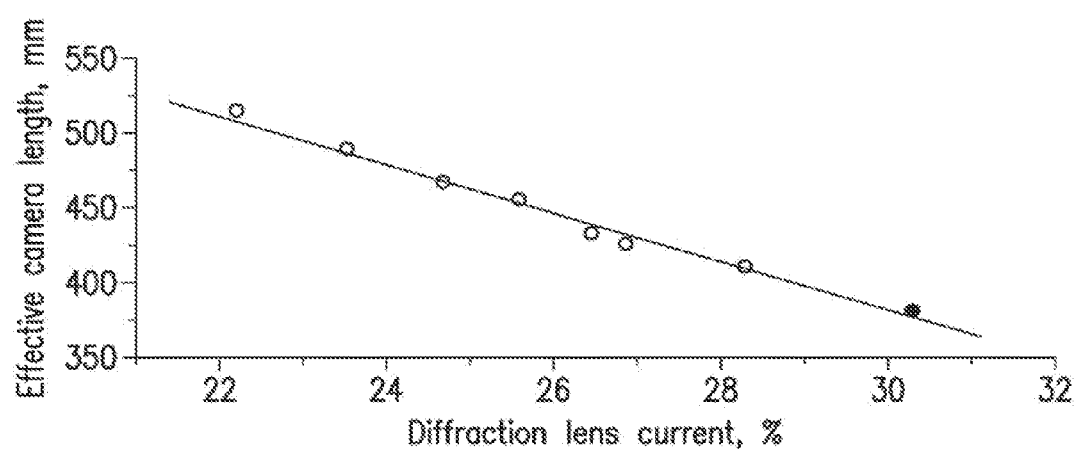

One way to compensate for the additional focusing is as follows: for a known standard material a set of diffraction patterns may be collected using diverse beam convergence. Each pattern is focused using the diffraction lens. Then, the interplanar distances seen on the patterns are measured and the effective camera length is calculated. As depicted in FIG. 11(c), this effective camera length shows a linear trend when plotted against the diffraction lens current value. A linear fit to the measured data can be used as a calibration curve for any nanodiffraction pattern. The final accuracy of camera length determination using this procedure has statistical character and is typically better than 2%.

Figure 12A:
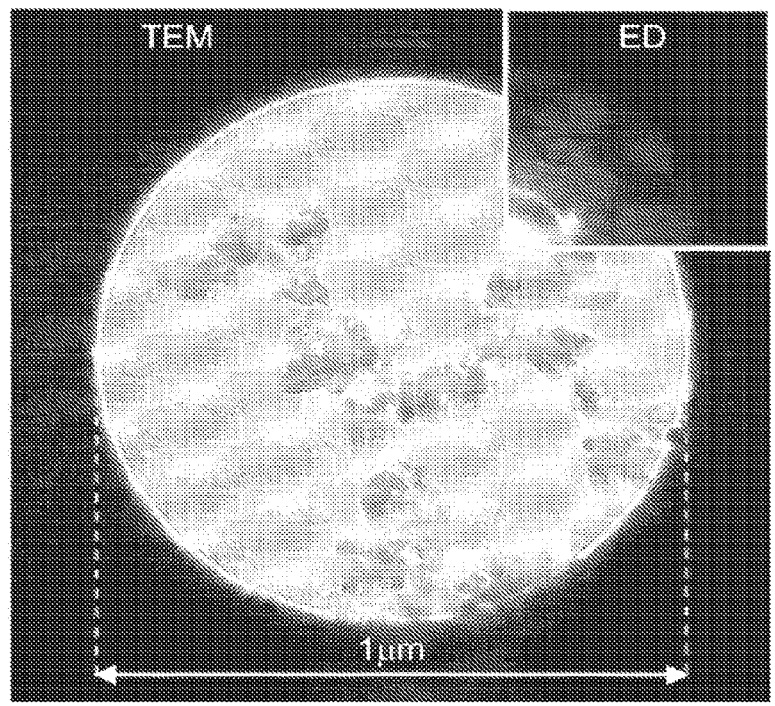
FIGS. 12A & 12B demonstrate TEM and STEM electron diffraction data acquisition on CuPcCl.
Figure 12B:
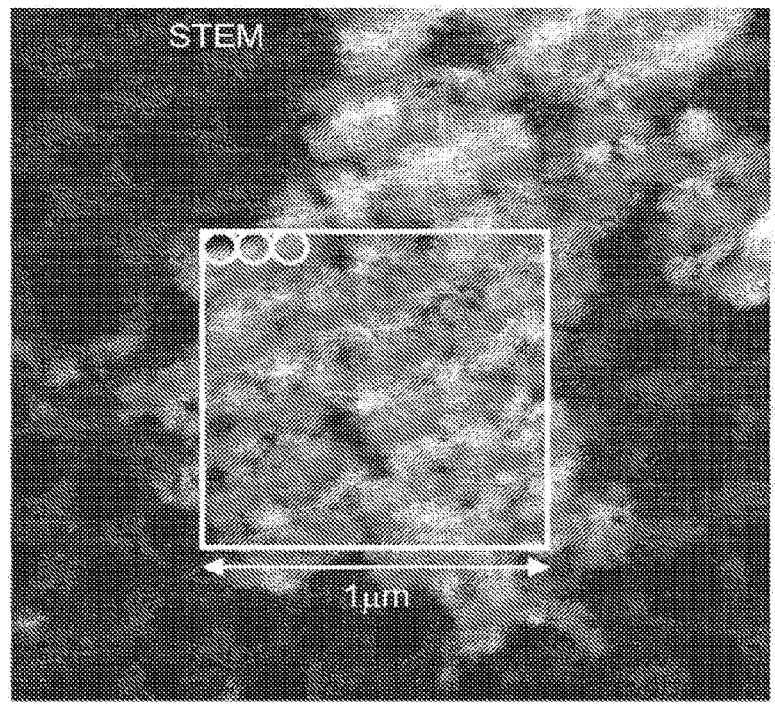

In the present disclosure, data were acquired at a medium magnification of 15,000× in TEM mode. The beam size was set to 1 μm diameter as depicted in FIG. 12(a). After the necessary alignments were completed, including eucentric height adjustment and beam size selection, a reasonably low illumination level of the beam was selected. The intensity of the beam is dictated by the radiation stability of the sample. Ideally, this critical electron dose that can be tolerated by the sample should be estimated as described above before diffraction data is collected for PDF analysis. Following this procedure it was determined that the electron dose rate during measurements for CuPcCl be kept at the level of 15 $e^-/Å^2 \cdot s$, and for β-CuPc and γ-QA at 0.7 $e^-/Å^2 \cdot s$. A slight convergence of the incident beam required additional focusing of the diffraction pattern. The effective camera length was determined using the calibration plot of FIG. 11(c) to be 415 mm (nominal 380 mm).

The stage was shifted mechanically in a grid in steps of 1 μm. At each stage position first an electron diffraction pattern was recorded with 1 s exposure time, then the image of the area was taken. The procedure can easily be automated according to methods known to those of ordinary skill in the art and delivers high quality data in a few minutes.

In total, 50 pairs of diffraction/image pairs were collected from each sample. This approach not only maximizes counting statistics while minimizing beam damage, but increases the powder statistics (the number of crystallites that are averaged over to obtain the integrated diffraction patter) in a natural way. Based on the corresponding images these pairs were classified into: (i) diffraction patterns from the material, (ii) diffraction patterns from the carbon film only, and (iii) diffraction patterns including copper grid parts. The patterns from the carbon film were averaged and used for background estimation; the patterns with copper reflections were discarded. All diffraction patterns from the material were summed together, and likewise for all the background diffraction patterns, and these integrated images were used for further processing. In alternative embodiments, the diffraction/image pairs may be further classified with respect to many alternative characteristics apparent to one of ordinary skill in the art. For example, diffraction patterns from areas of the sample with different visual appearances may be classified separately, thus allowing identification of multiple structural types within one sample. In another alternative embodiment, the presence of multiple structural types may be detected from comparison of the diffraction patterns themselves. This comparison may additionally involve statistical discrimination techniques known to those of ordinary skill in the art.

STEM/Nanodiffraction

In an alternative embodiment of the present disclosure, a particularly soft illumination setup can be realized by combining scanning transmission electron microscopy (STEM) imaging with nanodiffraction. STEMs with high-angle annular dark field (HAADF) detectors allow for obtaining very high contrast images of the sample, while keeping the effective electron dose low. Electron diffraction patterns in nanodiffraction mode can then be recorded from certain areas of the sample seen in the STEM image. This method is particularly beneficial for non-homogeneous samples.

Figure 3B:
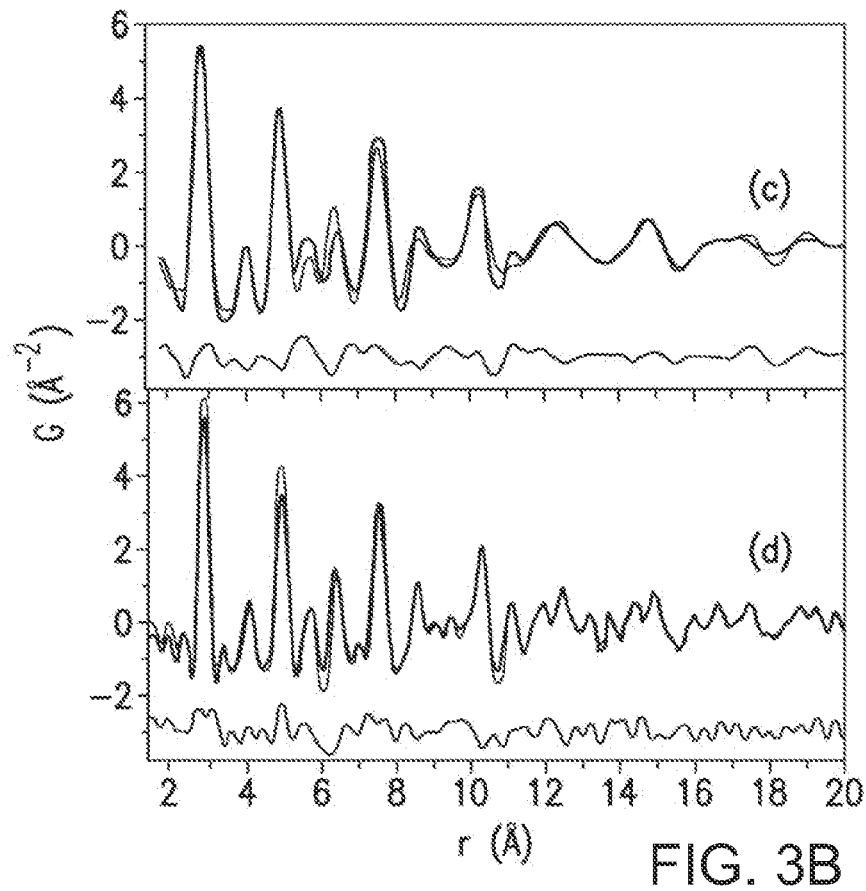

An automated acquisition module developed for a different application, automated diffraction tomography, ADT (Kolb et al., 2007; Kolb et al., 2008), provides the possibility to scan a certain area selected in a STEM image in diffraction mode. We used this module here to obtain data for our PDF study. Depicted in FIG. 3(b), the size of the scanned area was set to a square with a side length of 1 μm, and the beam size for nanodiffraction was kept at 100 nm. Thus 10×10 electron diffraction patterns could be collected without overlap in a 1 μm square. The electron dose rate for CuPcCl was 10 $e^-/A^2 \cdot s$, for β-CuPc and γ-QA at 0.3 $e^-/Å^2 \cdot s$, which is lower than the dose rates for the TEM mode. As for the data collection in TEM, the exposure for a single diffraction pattern was 1 s. Diffraction patterns for the background estimation were collected from an adjacent area that included no particles.

Data Reduction for Electron Diffraction

In a preferred embodiment the diffraction patterns can be recorded with the central beam shifted to a corner of the detector. The patterns were centered by analyzing the gradient of the central beam as described in Kolb et al., (2007). After the patterns were centered, several patterns from different parts of the sample, as described above, were averaged in order to increase the signal to noise ratio by improving the counting statistics and to improve the powder average. Averaged patterns were then azimuthally integrated and normalized by the number of 2D pixels fallen in to each bin of constant Q-value. The integration procedure was done by a home-written program and produced integrated intensity vs. Q. Elliptical distortion, often observed in electron diffraction patterns and typically below 2%, was neglected. The same procedure was applied for diffraction patterns recorded from the supporting holey-carbon film for background estimation.

X-ray Diffraction

For comparison with the electron diffraction patterns, X-ray powder diffraction data of CuPcCl, CuPc, and QA samples were measured in transmission geometry using a STOE Stadi-P diffractometer equipped with a Ge(111) monochromator and the silicon strip detector DECTRIS MYTHEN 1K. The samples were contained in sealed glass capillaries, which were rotating during the measurements to increase powder averaging. The data were recorded with Cu—$K_{\alpha 1}$ radiation (λ=1.5406 Å) in the 2θ range from 2° to 130°, which corresponds to a Qmax of 7.39 $Å^{-1}$. The step size was 0.01°, with a counting time of 100 seconds per 0.5° detector steps, resulting in a total counting time of 8 hours per sample. The background was determined by measuring an empty capillary under identical experimental conditions.

Obtaining the PDF

In the presently disclosed embodiment, the PDF was obtained from the integrated 1D diffraction patterns using a home-written program PDFgetE. This program subtracts background intensity and makes corrections for intensity aberrations in the data such as coming from sample absorption, incoherent multiple scattering and inelastic scattering. It normalizes the data by the average electron form factor of the sample and for the incident flux to obtain the properly normalized structure function, S(Q) and then F(Q). Finally it performs the Fourier transform of Equation 1 to obtain the PDF. The background intensity can be scaled and $Q_{max}$, the maximum value of Q over which data are used in the Fourier transform, can be varied by the user in such a way as to obtain the best possible PDF given the data. A public release of the program is planned for the future.

Modeling

PDFs can be calculated from structural models and it is common to optimize model parameters by updating them in such a way as to get a good fit of a calculated PDF to a measured one. A widely used program for doing this is PDFgui. For the β-CuPc sample we used PDFgui to calculate the PDF from single-crystal data from the literature. PDFgui is not adapted for refining structures from molecular systems and so we did not carry out structure refinements. However, certain profile parameters were adjusted to improve the agreement. These were scale-factor, $Q_{damp}$ (which accounts for the effects of the finite resolution of the measurement) and $S_{rat}$, a factor that sharpens PDF peaks at low r below a cutoff, $r_{cut}$. This mimics the effects seen in molecular systems that PDF peaks from intra-molecular atomic pairs tend to be much sharper than the peaks from the inter-molecular correlations.

EXAMPLES

The exemplary embodiments of the present disclosure described below demonstrate that quantitatively refinable PDFs can be obtained using widely available electron microscopes. Obtaining a good powder average can be an important part of powder diffraction regardless of the probing technique, XRD, ND or ED. This can be achieved by using a large sample volume in ND and by spinning the sample in XRD. However, in ED, both of these methods can be difficult due to the limitations of the configuration and should be achieved through sample preparation. Some modern TEMs have the ability to rock the sample, which can facilitate obtaining a good powder average. However, exemplary embodiments of the present disclosure can provide good ePDFs from a simple TEM, which can be found in many universities.

In order to differentiate between the different radiation sources, the present disclosure uses the names 'ePDF' for PDF from electron diffraction data ('xPDF': from X-ray data, 'nPDF': from neutron data) and 'eF(Q)' for F(Q) from electron diffraction data ('xF(Q)': from X-ray data, 'nF(Q)': from neutron data).

CuPcCl (Hostaperm® Green GNX), β-CuPc (Hostaperm® Blue B2G) and γ-QA (Hostaperm® Red E3B) were obtained from Clariant GmbH, Frankfurt. All three samples used were industrially produced nanocrystalline powders. Since ePDF generally lends its use for the analyses of nanocrystalline materials, the samples were used as received. TEM samples of CuPcCl, β-CuPc, and γ-QA were prepared by suspending the powders in n-hexane in an ultrasonic bath. A drop of the suspension was then placed onto a holey-carbon coated copper grid and dried in air.

As described, the ePDF can be a favorable situation for nanomaterials. The nanoparticles in a material are typically single crystals. Therefore, even a small volume of a nanosample can have enough randomly oriented particles to give a good powder average. And bulk materials can be ball-milled to obtain nanoparticles for ED. However, ball milling can cause-induced strain and damage to the crystals. This damage may be repaired by annealing samples before taking ED measurements. Preferably, the experimentalist will take care to obtain a thin enough layer of sample to avoid multiple scattering. A sample may be suspended in ethanol or acetone and a dropper or a pipette can be used to obtain a thin layer of sample on a holy carbon grid. Focusing on the edge of a particle cluster can be another approach to choose a thin area for ED, though there can be a danger that this may not be representative of the sample. Inelastic scattering components can be eliminated, for example, by using omega filters and this should improve the data quality for PDF analysis. However, useful PDFs can be obtained without filtering.

The attainable $Q_{max}$ is usually determined by the operational energy, camera length, dimensions of the detector and the diameter of the microscope. However, most of the electron microscope configurations equipped with a CCD camera limit attainable $Q_{max}$, somewhere around ~17-18 Å. The advantage of using a higher $Q_{max}$ can be that the better real space resolution that results in the ePDF. The available $Q_{max}$ can be limited by the electron energy, diameter of the microscope and diameter of the microscope column.

Example 1

Gold Film

FIG. 2(a) shows a TEM image of the gold film that was analyzed in the present example. The CCD image of the diffraction pattern from the Au film is shown, for example, in FIG. 2(b). The rings appear smooth and uniform suggesting that there can be a good powder average. The resulting integrated ID patterns shown in FIG. 2(c) are smooth and have good statistics. This is further borne out in the F(Q) functions shown in FIG. 3(a). The statistics compare favorably to the F(Q) derived from x-ray data shown in FIG. 3(b). The two reduced structure functions are similar in peak positions and intensities, suggesting that in this exemplary case the scattering in the ED experiment is kinematical. The resolution is lower in the ED data, and the features in the scattering can die more quickly with increasing-Q, than the x-ray data. The latter is likely to reflect real differences in the samples. The lower resolution can be either a sample or measurement effect. By comparing FIG. 3(c) and (d), it can be seen that there is a high degree of similarity between the exemplary ePDF and the corresponding xPDF, albeit the exemplary ePDF peak can be broader than those for the xPDF. This shows that, in the case of polycrystalline Au films of 2:7 nm thickness, kinematical PDFs can be obtained from ED. The sputtered gold film has an fcc gold structure, like the bulk, but with more disorder and a nanometer range for the structural coherence.

The ED data were taken with a standard CCD camera and no filtering of inelastically scattered electrons. This can be a straightforward protocol for data collection, as it can be the standard setup in most laboratory TEMs. It can be expected to result in lower quality PDFs than those measured with energy filtered electrons because of the higher backgrounds from inelastically scattered electrons. Electron diffraction data collected with an image plate detector can also be expected to be higher quality due to the low intrinsic detector noise and better dynamic range of that detector technology. Thus, the resulting exemplary PDF shown in FIG. 3(c) represents the baseline of what can be possible without specialized instrumentation. The resulting F(Q) shows excellent signal to noise up to the maximum accessible Q-range of 18 Å$^{-1}$, as evident, for example, in FIG. 3(a).

Exemplary results of the model fitting are shown in Table I. The structure model used was fcc gold bulk structure, space-group Fm-3m. It was not possible to measure the nanoparticle size from the ePDFs as we were not able to calibrate the intrinsic Q-space resolution of the ED measurement and separate the instrumental resolution and particle size effects in the ePDFs. The quality of the fits to the exemplary ePDF are comparable, for example, to those to the xPDF NP data. Fits to NP data-sets can result in worse agreement factors, $R_w$, than corresponding fits to bulk materials (Masadeh et al., 2007; Tian et al., 2011). This can be because of structural modifications in the NPs that may not be in the PDFgui models such as, e.g., relaxation at NP surfaces, bond-length relaxations throughout sample (Jadzinsky et al., 2007), planar defects, and non-spherical particle shapes. Correspondingly, a somewhat poor, but acceptable $R_w$=0.20 is obtained for the xPDF data. It is thus promising that a comparable $R_w$=0.17 for the fit to the Au NP ePDF can be found. The exemplary ePDF is of high-enough quality to attempt quantitative PDF refinements to it despite the possible distortions described above. This is borne out by the similar values refined for structural parameters from the two datasets (see, e.g., Table I).

TABLE 1

| | ePDF (film) | ePDF (NP) | xPDF |
|---|---|---|---|
| Qmax (Å$^{-1}$) | 15.25 | 15.25 | 15.25 |
| Fit range (Å) | 1-20 | 1-20 | 1-20 |
| Cell parameter (Å) | 4.075(3) | 4.076(2) | 4.058(1) |
| $U_{iso}$ (Å$^2$) | 0.033(4) | 0.006(3) | 0.014(1) |
| Diameter (Å) | ~27[a] | ~1000[b] | 24.51(9) |
| Q-damp (Å$^{-1}$) | 0.095(5) | 0.095(5) | 0.047(2) |
| $R_W$ (%) | 17 | 24 | 20 |

[a] film thickness measured during deposition
[b] NP diameter estimated directly from the TEM image Example 2

Gold Nanoparticles

Figure 4A:
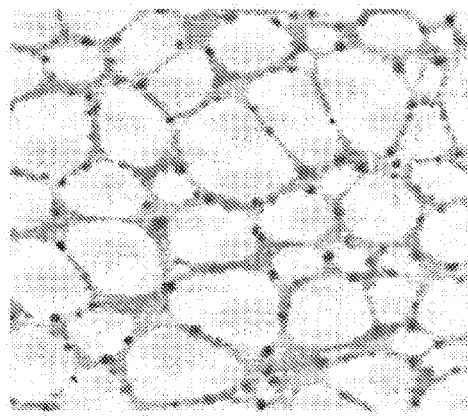
FIGS. 4A-C depict TEM and ED data for 100 nm Au nanoparticles.
Figure 4B:
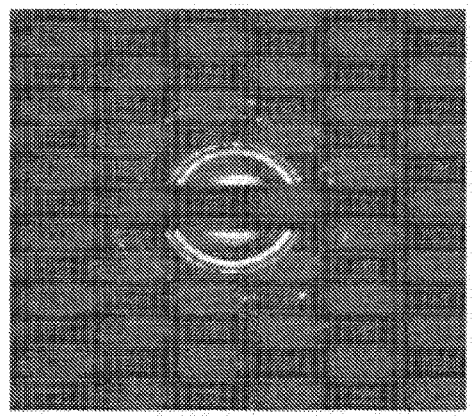
Figure 4C:
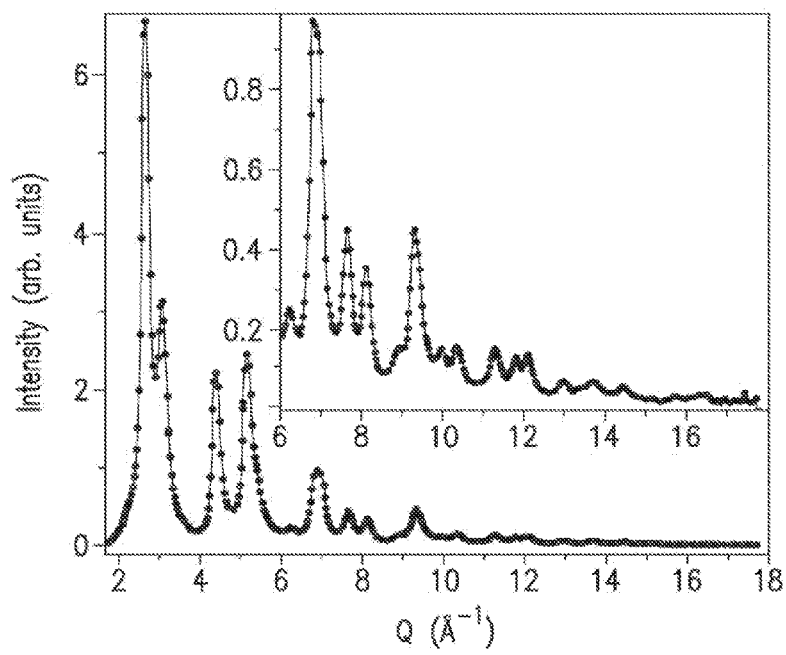

To explore the size limits for Au NPs to scatter kinematically, data can be collected, for example, from larger, 100 nm Au nanoparticles. A TEM image of the sample is shown, for example, in FIG. 4(a). The black dots are the gold nanoparticles supported on the carbon grid. An exemplary CCD image of the ED pattern from this sample is shown in FIG. 4(b) and the integrated 1D diffraction pattern of this image is shown in FIG. 4(c). A small amount of granularity on this ED image can be observed due to an imperfect powder average. Even in the kinematical scattering regime, this can affect relative Bragg peak intensities.

Figure 5A:
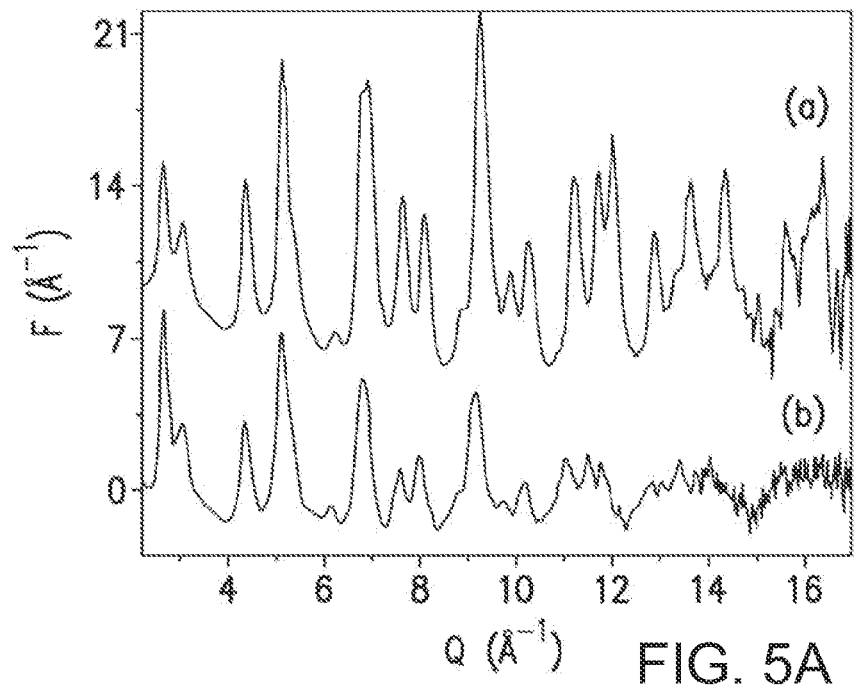
FIGS. 5A & 5B depict RSFs and PDFs of 100 nm Au nanoparticles, measured with both electron and x-ray diffraction.
Figure 5B:
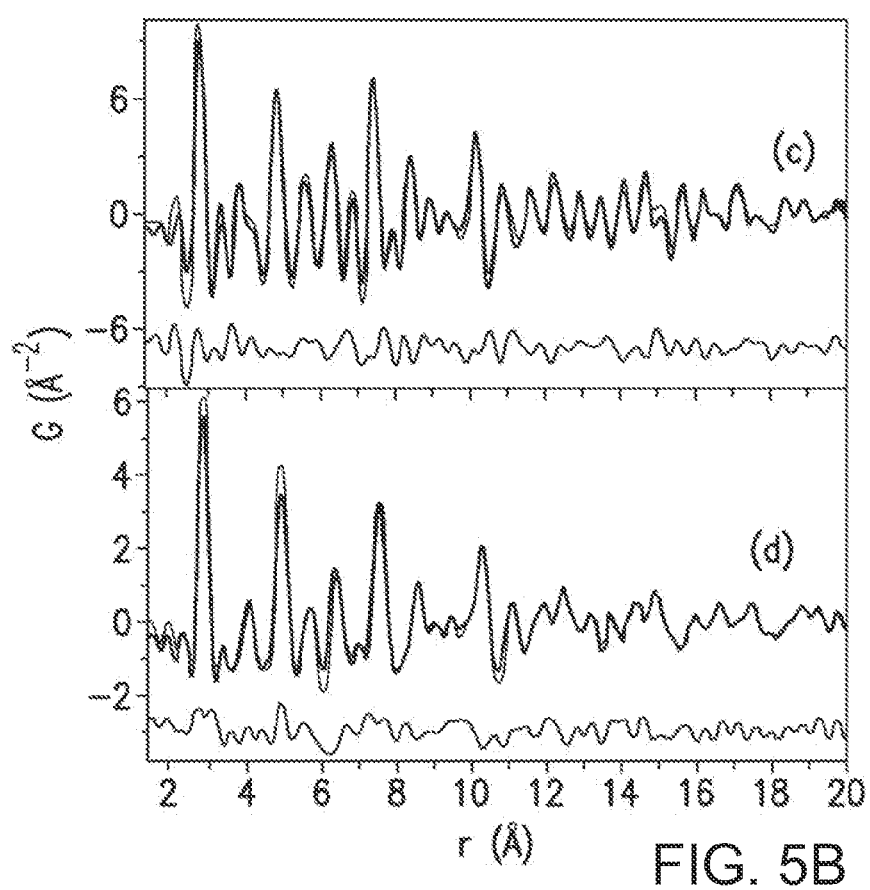

Comparing the integrated 1D diffraction patterns of the large NPs and the thin Au film (e.g., FIGS. 4(c) and 2(c), respectively) similar features can be seen, but in the case of the NPs, the amplitudes of the scattered intensities extend to higher Q values, as if there is a smaller Debye-Waller factor (DWF) for the data. This can be observed in the reduced structure function from this data set F(Q) given, for example, in FIG. 5(a). For comparison, a reduced structure function obtained from the x-ray data set is also presented, for example, in FIG. 5(b). The enhancement in the high-Q features can be large and can be due to significant coherent multiple scattering in this sample. The resulting ePDF from the NPs has peaks that are correspondingly sharp compared to the thin film gold and the xPDFs of gold NPs.

Regardless of the observed differences, a model can be refined against the ePDF of the 100 nm Au nanoparticle layer to see the extent that the refined structural model parameters can be affected. The structure refinement gives fits that were comparable in quality to the xPDF fits (see, e.g., Table I), $R_w$=0.24. The refined values can be similar also, except the ADPs that were smaller for the fit to the ePDF data, due to, for example, the artificially sharpened peaks. It is somewhat remarkable that, in this exemplary case, the dynamical scattering produces features in the F(Q) with approximately the correct relative amplitude, but extending to much higher-Q. Gold is a special case because the structure factors can be either ones or zero's.

Example 3

Sodium Chloride Film

A more complicated structure factor is obtained from binary compounds, such as the NaCl film studied using certain exemplary embodiments of the present disclosure, obtained by a radio-frequency thermal evaporation method.

Figure 6A:
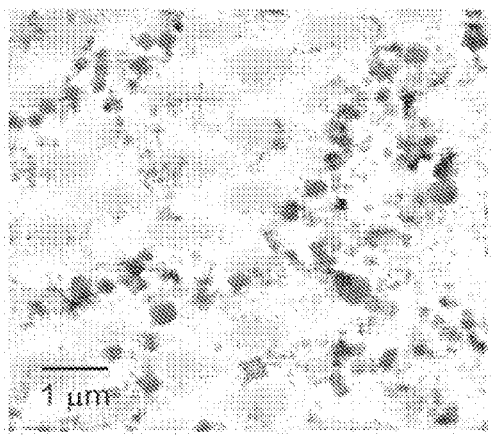
FIGS. 6A-6C depict TEM and ED data for a NaCl film.
Figure 6B:
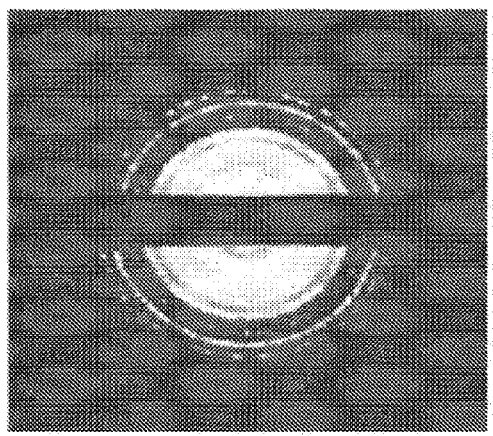
Figure 6C:
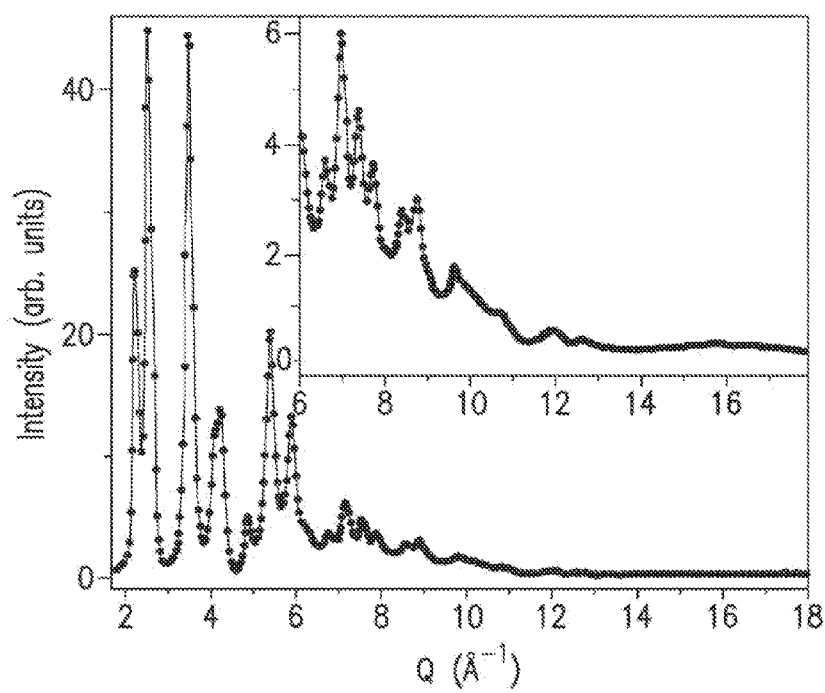
Figure 7A:
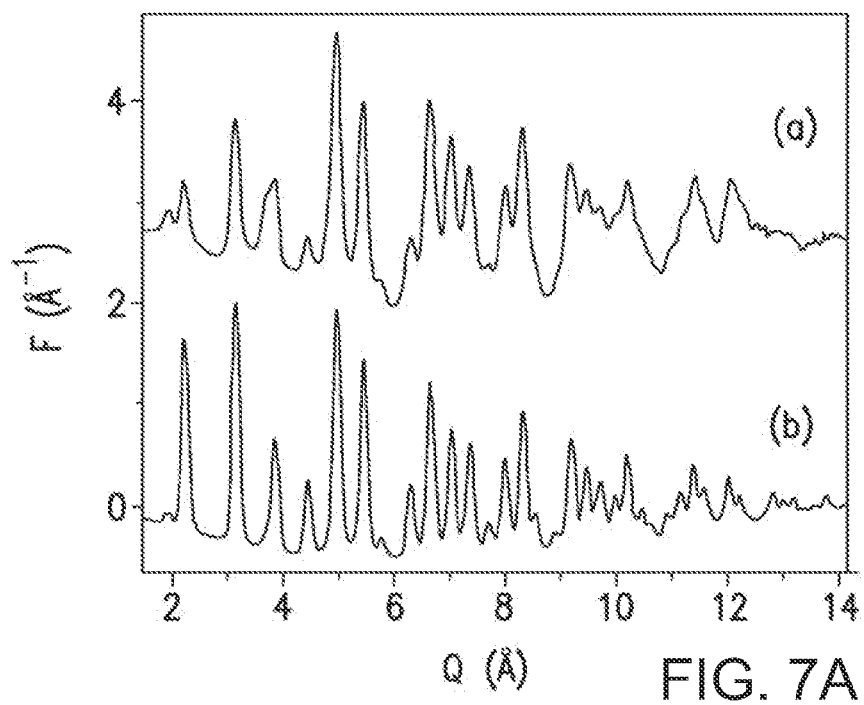
FIGS. 7A & 7B depict RSFs and PDFs of a NaCl film, measured with both electron and x-ray diffraction.

The TEM image of the sample in FIG. 6(a) shows, for example, that it includes nanoscale grains, some of which have a cubic shape and others that have no particular morphology. The corresponding ED pattern in FIG. 6(b) shows fairly uniform rings, with some spottiness from an imperfect powder average. FIG. 6(c) shows the integrated ED pattern. The F(Q) and the resulting exemplary ePDF obtained from this data set is shown in FIGS. 7(a) and (b), respectively. For comparison, an xPDF obtained from a bulk crystalline NaCl sample is also shown in FIG. 7(c).

Figure 7B:
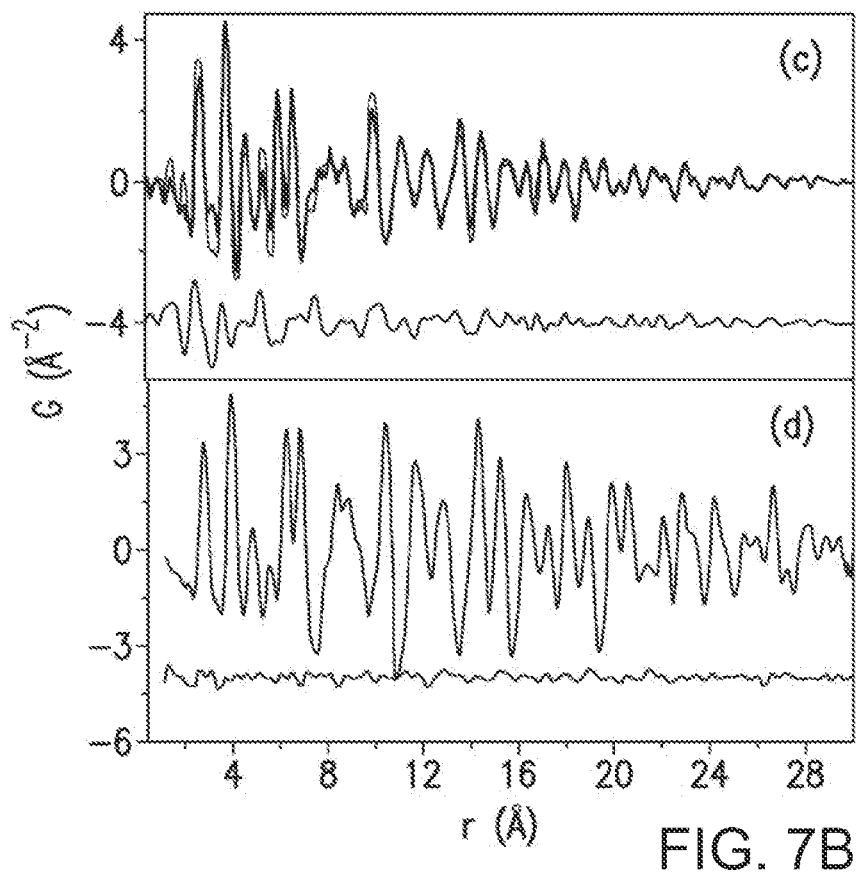

The fits of the bulk NaCl model to the data are presented in FIGS. 7(b) and (c) and the results are presented in Table II. The ePDFs and xPDFs are qualitatively highly similar, with the features in the xPDF recognizable in the exemplary ePDF. Notably, the relative intensities of adjacent peaks can be similar between the e- and xPDFs suggesting kinematical scattering. Peaks in the exemplary ePDF can die out in amplitude with increasing r more quickly, due to the broader features in the electron diffraction pattern, presumably an instrumental resolution effect. The exemplary results of the fits of the rock-salt structure to the PDFs are presented, for example, in Table II and FIGS. 7(b) and (c). The overall quality of the fits to the exemplary ePDFs is worse than the xPDFs of bulk NaCl. Refined lattice constants agree within experimental uncertainty. The refined thermal parameters are smaller than those measured from the x-ray data. This is unlikely to be a real effect as both the x-ray and electron data were measured at room temperature, and it is rather implausible that the nanoparticulate samples have less structural static disorder than bulk NaCl. Accordingly, this may be the effect of multiple scattering in the data. ADPs refined from ePDFs can present a lower bound on actual sample ADPs. They can be accurate in the case where multiple scattering is negligible, but can underestimate the thermal motions in the presence of multiple scattering.

TABLE II

NaCl ePDF and xPDF modeling parameters

| | ePDF | xPDF |
|---|---|---|
| Qmax Å$^{-1}$ | 11.4 | 11.4 |
| Fit range Å | (0.2-30) | (0.2-30) |
| RW % | 3 | 6 |
| Q-damp | 0.095(5) | 0.06(1) |
| Cell parameter Å | 5.62(2) | 5.63(1) |
| $U_{iso}$ - Na | 0.007(5) | 0.027(1) |
| $U_{iso}$ - Cl | 0.004(4) | 0.016(1) |

Example 4

Black Mercuric Sulfide

Figure 9A:
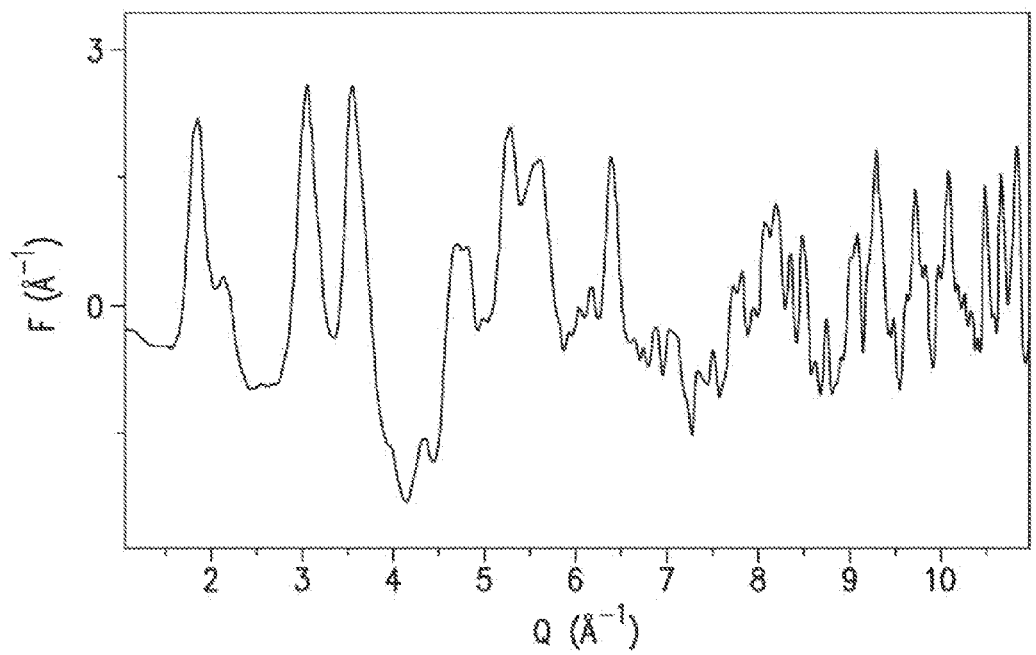
FIGS. 9A & 9B depict RSFs and PDFs of HgS nanoparticles, measured with electron diffraction.
Figure 9B:
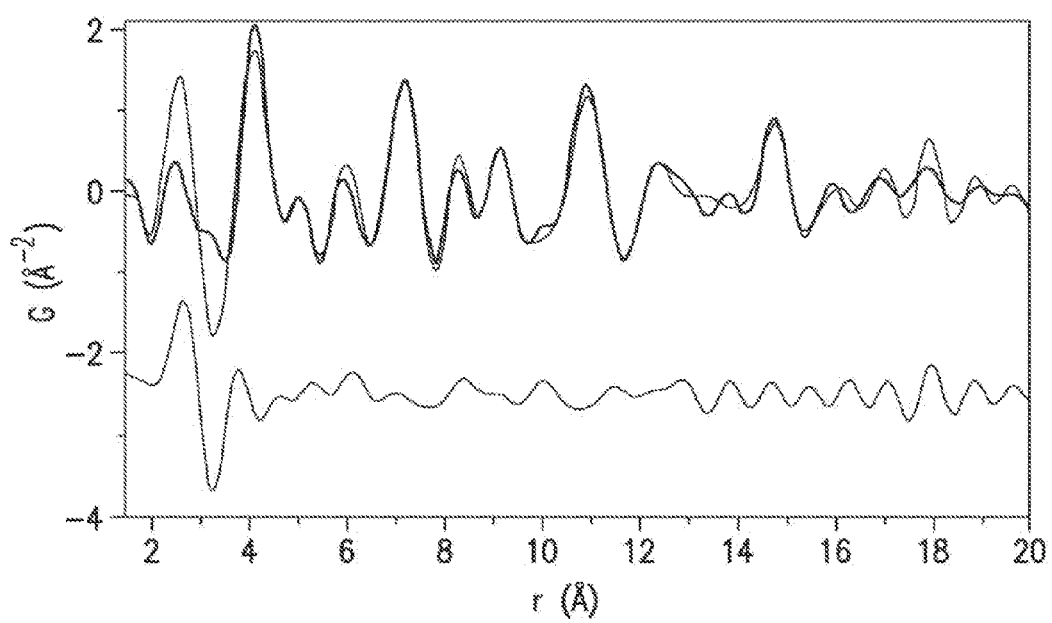

To evaluate the performance of the exemplary ePDF for samples where the atomic numbers of the constituents can be different, β-HgS (Black) can be considered. An exemplary TEM image of the sample is presented in FIG. 8(a). The HgS-black sample has a good powder average, which is evident in FIG. 8(b). However, the statistics of the measurement are poor. This may be due to absorption by the sample. Apart from a low-r aberration in the HgS PDF, there is a good fit to the data (FIG. 9(b)) of the structural model. Due to the poor statistics, a low Qmax=9 Å was used. It is not clear why the scattered signal was weak since Hg is usually a strong scatterer. It can be, for example, that the material is highly disordered resulting in a weak coherent signal, or that the sample was too thick and there was insufficient penetration. The exemplary refinement results from this sample are presented in Table III.

TABLE III

HgS nanoparticle ePDF modeling results

|  | β-HgS |
|---|---|
| Qmax Å$^{-1}$ | 9 |
| Q-Damp | 0.095(5) |
| R$_W$%: Fit range (1.2-20) Å | 44 |
| R$_W$%: Fit range (3.5-20) Å | 23 |
| a Å | 5.800(8) |
| U$_{iso}$ - Hg | 0.036(6) |
| U$_{iso}$ - S | 0.02(2) |

Example 5

Chlorinated Copper Phthalocyanine (CuPcCl, Pigment Green 7)

Figure 13A:
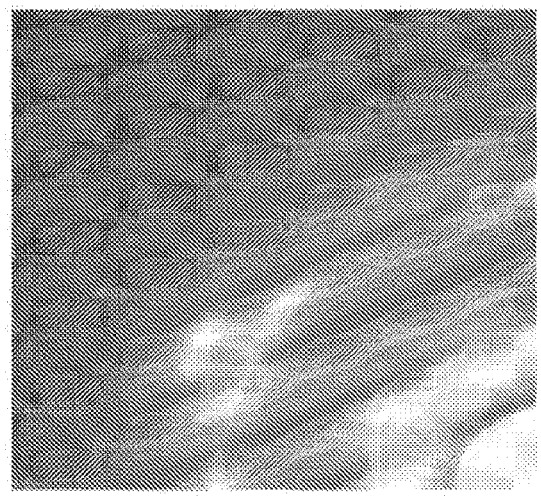
FIGS. 13A-13C depict false-color images of the electron diffraction patterns from the CuPcCl sample.
Figure 13B:
Figure 13C:
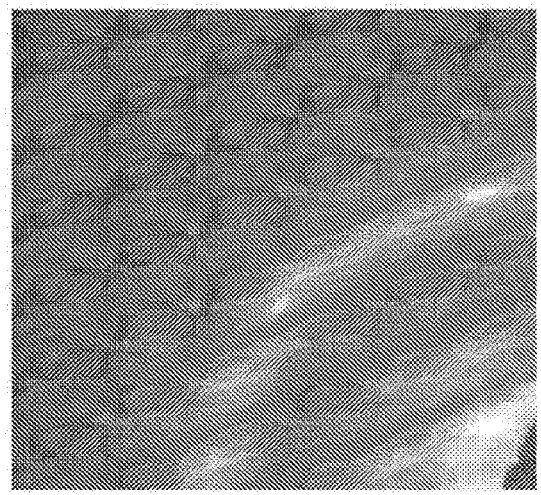

FIG. 13 shows the summed electron diffraction patterns from CuPcCl obtained using the TEM/nanodiffraction mode. The direct beam is in the lower left hand corner of the image. Debye-Scherrer powder diffraction rings are clearly evident in the raw data of FIG. 13(a), though there is some distortion apparent along a radial direction at around 30° to the vertical. This aberration is a ghost image of the electron source and it appears also in the background pattern shown in FIG. 13(b). FIG. 13(c) shows the data of (a) after subtracting the background. There is a small intensity modulation along the rings indicating an imperfect powder average, which is mitigated somewhat after the azimuthal integration into a 1D profile.

Figure 14A:
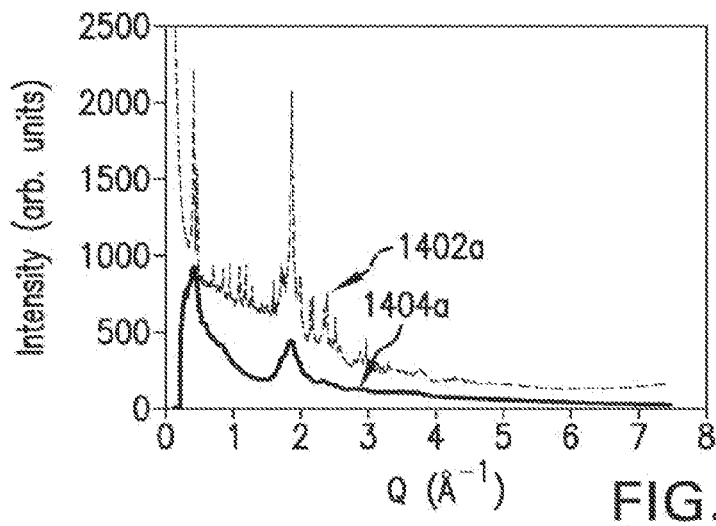
FIGS. 14A-14C show a comparison of electron diffraction and X-ray diffraction data of CuPcCl.

Azimuthal integration of the background-subtracted image results in curve 1404a in FIG. 14(a). In comparison, curve 1402a in FIG. 14(a) shows data from the same sample collected using Cu K$_{\alpha1}$ X-rays. Although the electron diffraction data has much lower resolution than the X-ray data, the same overall features are evident though significantly broadened in the electron diffraction data. This is usually a good trade-off for PDF work, where currently the method of choice for X-ray PDF measurements is the low resolution but high throughput rapid acquisition PDF (RAPDF) mode.

The main effect of the lower Q-space resolution is a loss of PDF peaks in the high-r region, often beyond the range that is analyzed by modeling or fingerprinting. The electron diffraction data are also seen to fall-off at low-Q. This is due to overexposure of the area in the centre of the transmitted beam: the detector pixels are saturated both for the diffraction pattern from the material and "empty" patterns for background. The subtraction of these overexposed areas produces regions with zero-intensity. Again, this does not affect the resulting PDF too adversely.

Figure 14B:
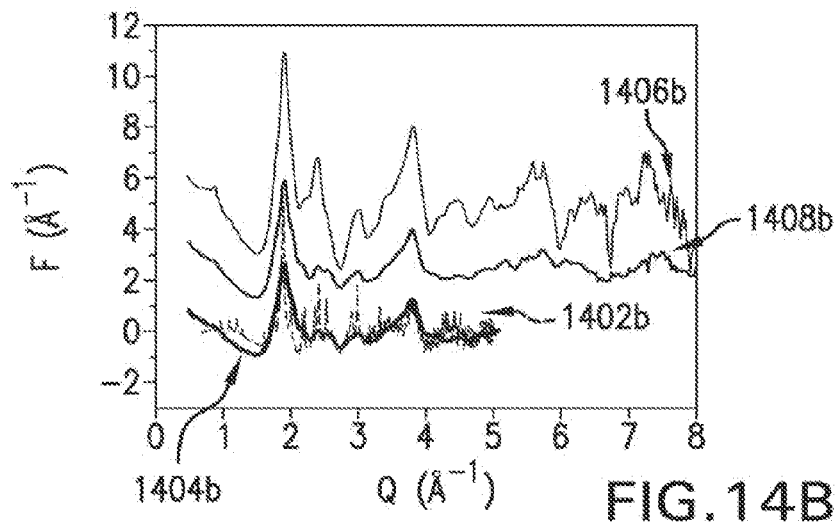

When the data in FIG. 14(a) are processed according to the methods described herein and known to those of ordinary skill in the art, F(Q) curves 1404b (electron) and 1402b (X-ray) in FIG. 14(b) are produced. It is now apparent that the electron and X-ray curves contain the same features, albeit at a different resolution. The limitation of the X-ray measurement is also apparent: although the data were collected for 8 hours, the statistics in the high-Q region are very poor, requiring that the data be terminated at a very low value of 5 Å$^{-1}$. On the other hand, despite being measured for much less time (1 second exposure time per diffraction pattern, in this data 37 patterns were averaged) the electron data have much better statistics in the high-Q region, as shown by the curve 1408b, which shows the same TEM/nanodiffraction data plotted further out to 8 Å$^{-1}$. Curve 1406b is another eF(Q), obtained using the STEM nano-diffraction approach described above. Again, the positions and relative amplitudes of the features are well reproduced, and in this mode we see that the Q-space resolution of the measurement is in fact a little higher than the TEM/nanodiffraction data. Clearly, both TEM and STEM nanodiffraction produce quantitatively reliable F(Q) functions from the CuPcCl sample.

Figure 14C:
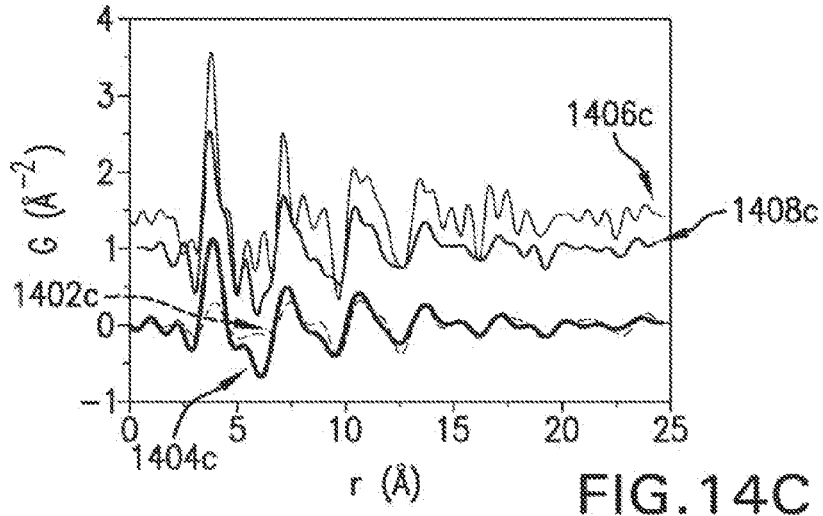

Finally, in FIG. 14(c), the PDFs from the datasets shown in 14(b) are plotted. Curves 1404c (ePDF) and 1402c (xPDF) may be compared directly as they were processed with the same Qmax of 5 Å$^{-1}$. They reproduce each other very well. The curves have been scaled to emphasize the overlap in the high-r region. This scaling means the low-r peaks have different amplitudes between the ePDF and xPDFs. This is a result of the differences in resolution between the techniques and is not a fundamental deficiency of the ePDFs.

Because the eF(Q)s have good statistics to a higher value of Q it is possible to obtain ePDFs with a higher Qmax of 8λ$^{-1}$ as shown by curves 1406c and 1408c, of FIG. 14(b), which were generated from curves 1406b and 1408b, respectively, in FIG. 14(b). They have all the same features as the lower-Qmax PDFs (curves 1402c and 1404c), but the peaks are sharper and it is possible to resolve features that are not evident in the low-Q PDFs.

This clearly demonstrates that it is possible to obtain quantitatively reliable ePDFs from organic materials.

Example 6

Copper-Phthalocyanine (CuPc, Pigment Blue 15:3)

Figure 15A:
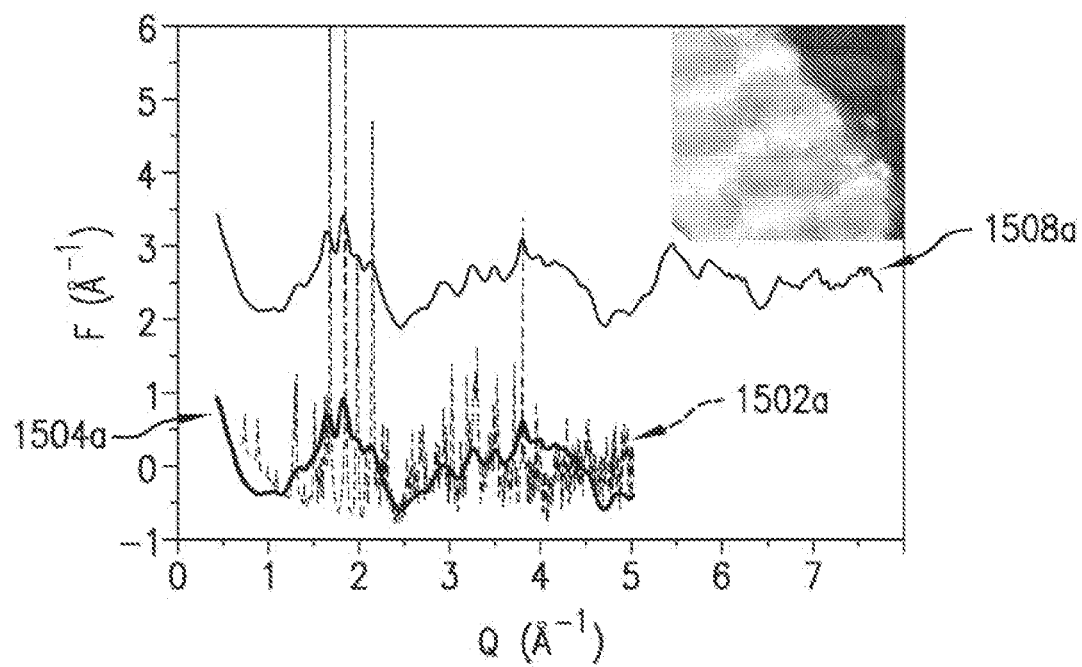
FIGS. 15A & 15B shows a comparison of electron and X-ray diffraction data for β-CuPc.

The results for the β-CuPc compound are shown in FIG. 15. The experiments and data analysis were more difficult in this case because of the beam sensitivity of the sample. The inset of FIG. 15(a) shows the background-subtracted diffraction pattern taken in the TEM/nanodiffraction mode is shown in the inset. The powder rings are smooth although a little spotty, indicating that there is some crystallinity in the sample.

The curves in FIG. 15(a) shows the data after 1D integration and converting to F(Q). Again, the eF(Q) (curve 1504a) and the xF(Q) (curve 1502a) from the laboratory X-rays are shown for comparison. The main features of the X-ray curve are reproduced in the eF(Q); the X-ray pattern has much poorer statistics, especially as Qmax of 5 Å$^{-1}$ is approached. The electron data, shown offset above in curve 1508a, extended all the way to the maximum Q-range measured of 7.7 Å$^{-1}$; features in the data are clearly evident all the way out, measured with good statistics. This presents us with the opportunity to obtain a PDF with better real-space resolution by Fourier transforming over this wider range.

Figure 15B:
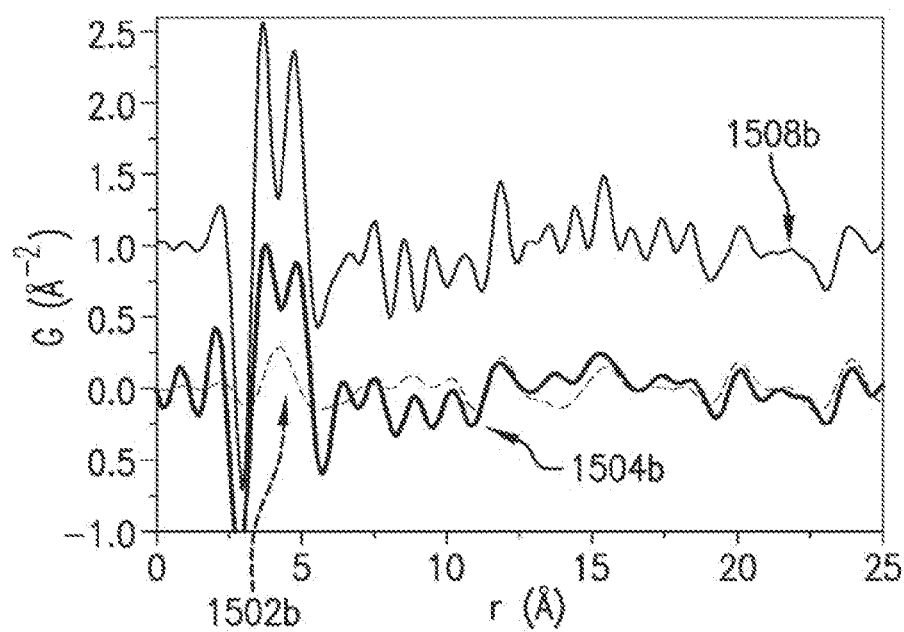

The resulting PDFs are shown in FIG. 15(b). Curve 1504b is the ePDF transformed with the same Qmax as the xPDF, which is curve 1502b. The features are all well reproduced, though as before we have scaled the ePDF to emphasize the good agreement in the high-r region and as a result the low-r peaks are suppressed in the xPDF. Nonetheless, they are well reproduced in position and relative intensity, apart from the faster drop-off in amplitude in the ePDF due to the lower Q-resolution of the measurement. The ePDF obtained with Qmax=7.7 Å$^{-1}$ (curve 1508b) has sharper, more well-resolved features and is a superior PDF of CuPc.

Figure 16:
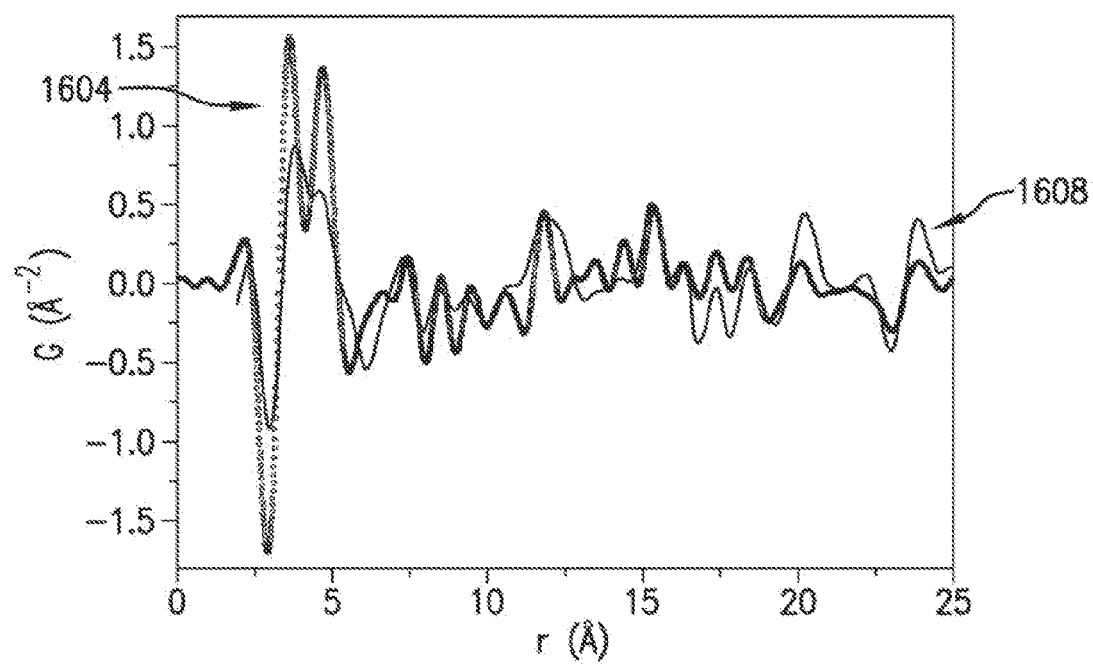
FIG. 16 shows a comparison of the ePDF (1608) with a calculated PDF from the known crystal structure of β-CuPc (1604).

FIG. 16 demonstrates a comparison between the best ePDF of β-CuPc, obtained using a Qmax of 7.7 Å$^{-1}$ from the TEM/ nanodiffraction data (curve 1608) and the PDF calculated from a model of the crystal structure determined from single-crystal data (curve 1604; Brown, 1968). The features of the curves are reproduced very well, especially considering that no true "fit" of the data varying the structural parameters have been done. Rather, the PDF was calculated from the model and parameters that account for scale-factor, $Q_{max}$ effect and resolution damping were applied to the calculated PDF to give a better overall agreement. The purpose of this exercise is not to obtain a quantitative fit to the data, which is not possible at the present time because of limitations of the fitting program, PDFgui, for fitting molecular solids, but to show that the ePDF obtained from the electron diffraction data is well reproduced by a PDF calculated from the known structure of the material.

Example 7

Quinacridone (QA, Pigment Violet 19)

Figure 17A:
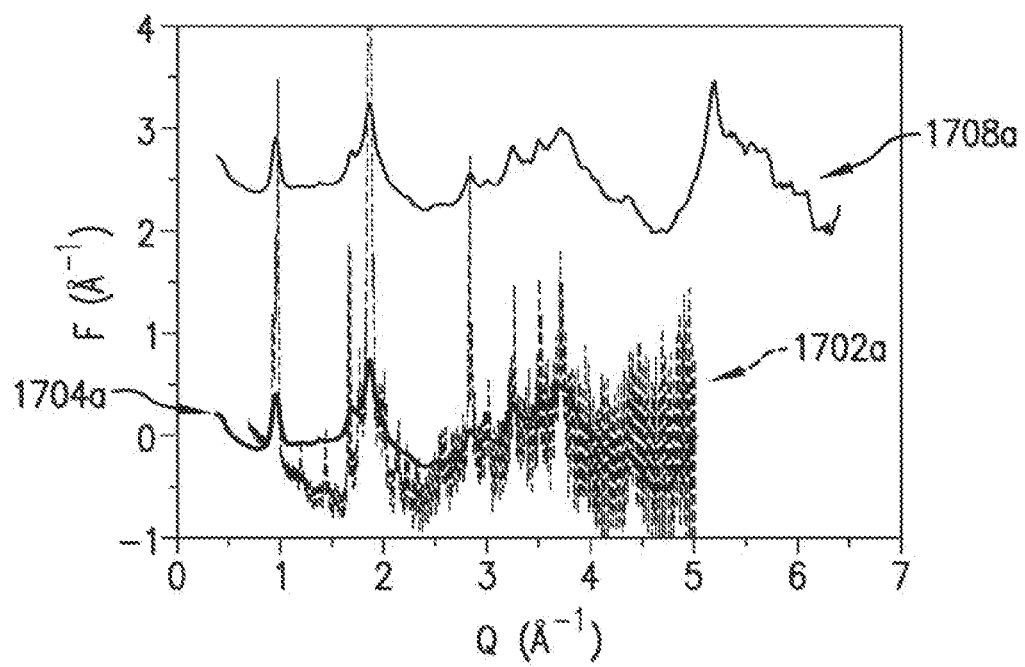
FIGS. 17A & 17B show a comparison of electron and X-ray diffraction data for γ-QA.
Figure 17B:
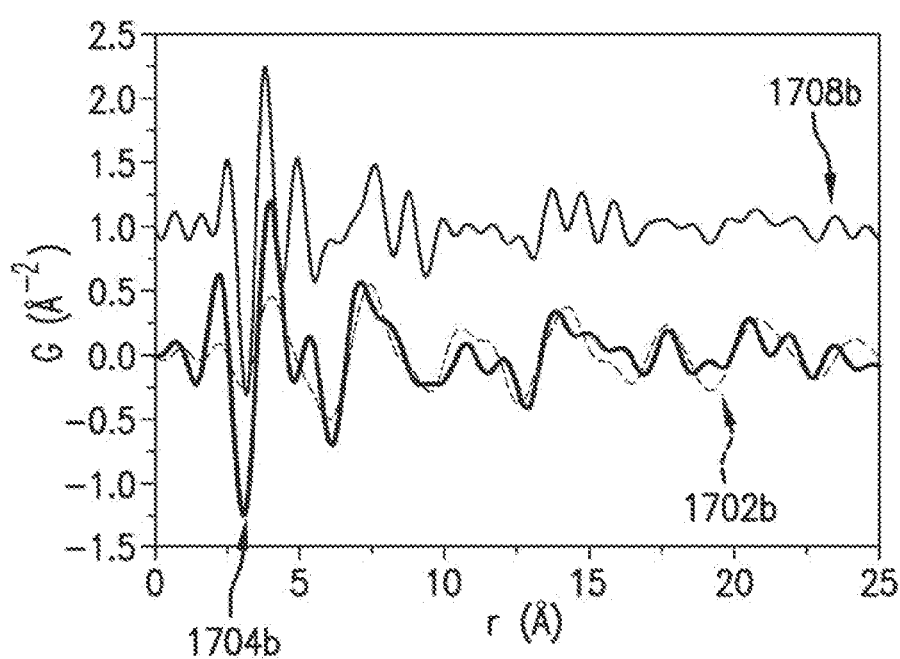

Quinacridone is an example of a purely organic compound that is also beam-sensitive. However, we demonstrate that this approach yields ePDFs that are of comparably high quality as shown for the CuPc phases discussed above. Averaged and background subtracted electron diffraction patterns of γ-QA were similar to those of β-CuPc-spotty powder rings. FIG. 17(*a*) shows the eF(Q) functions from TEM/nanodiffraction data (curves 1704a and 1708a, respectively) plotted on top of the X-ray F(Q) (curve 1702a). Apart from the lower resolution of the electron data there is a very good agreement. This is also evident when the data are Fourier transformed to the PDFs, as depicted in FIG. 17(*b*). This example shows that ePDF is possible for purely organic compounds, too.

Figure 18:
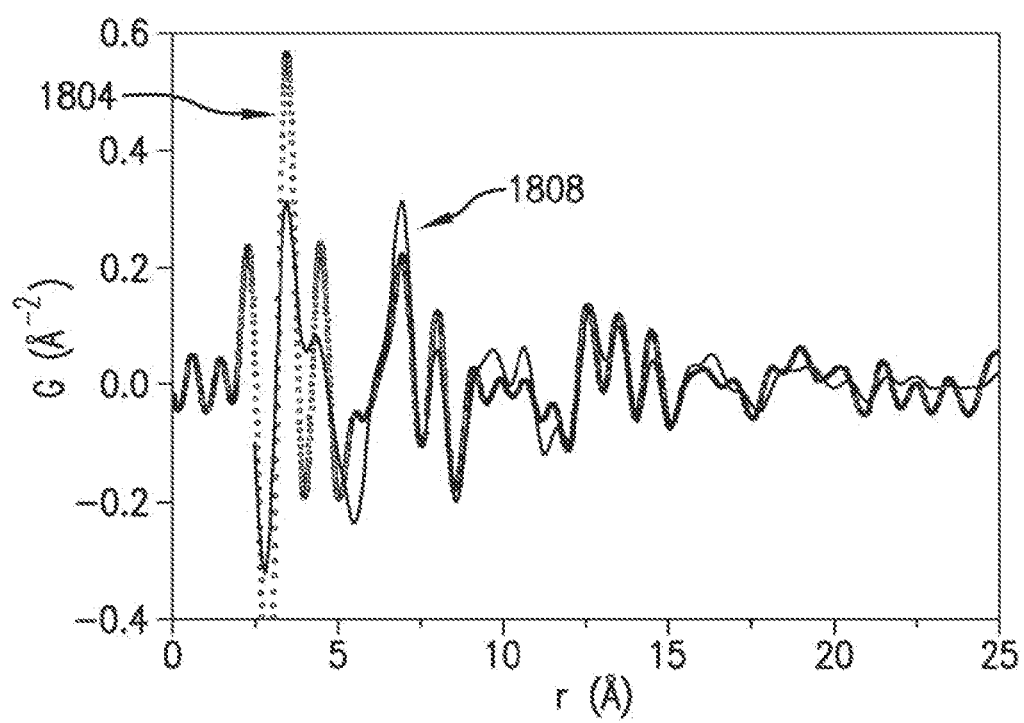
FIG. 18 shows a comparison of the ePDF (1808) with a calculated PDF from the known crystal structure of γ-QA (1804).

FIG. 18 shows a comparison between the ePDF for γ-QA (curve 1808) and a PDF calculated from the known crystal structure (curve 1804; Paulus et al., 1989). Again, although the structure model is not being fitted to the data the features of the two curves are very well reproduced giving further proof that the electron diffraction approach we have taken results in quantitatively reliable PDFs.

Comparison of PDF Obtained from Different Methods for Recording the Electron Diffraction Data The best strategy to minimize electron beam induced damage effects to the structure is to acquire data from fresh unexposed areas. This can either be achieved by a controlled stage shift or beam shift after each exposure. Mechanically controlled stage shift is more efficient for relatively large steps and therefore can be best used combined with a large illumination spot in TEM mode. The large beam size covers more particles and therefore increases the powder average of the diffraction data. SAED (selected area electron diffraction) using the SA (selected area) aperture limiting the area of interest can be used when a large beam size is necessary in order to keep proper geometry of the diffraction experiment, but small features of the sample (included in the SA aperture) have to be separated. Using this diffraction geometry one should keep in mind that the area not included in the SA aperture but illuminated during the exposure should not be used for data collection. In the nanodiffraction geometry all illuminated area is used for the data collection. Electron diffraction data collected using the stage shift is easy to realize experimentally and generally should result in better statistically averaged diffraction data.

Beam shift can be used for shorter shift distances. It can be most efficiently combined with STEM imaging mode. The STEM/nanodiffraction combination is a more sophisticated experiment and requires a dedicated acquisition module controlling the beam shift. Since it averages the diffraction data over a smaller area, it has generally poorer statistics as the TEM/stage shift approach with the large beam size. Nevertheless, since the diffraction data is collected from known positions within the STEM image, non-uniform samples can be analyzed.

Comparison of Different Electron Diffraction Setups for Determining the PDFs

Our experiments indicate that it is much easier to get good statistics on the data, both counting statistics and powder average, using the large beam size realized in TEM/nanodiffraction mode, than fine scanning in STEM/nanodiffraction. The latter works too, as shown in the CuPcCl, where high-quality PDFs were obtained in the STEM/nanodiffraction mode. However, significantly more averaging must be done in the STEM/nanodiffraction mode in order to get sufficiently well averaged data. This may still be attractive for non-uniform beam sensitive samples as particular area of the sample can be selected for sampling in STEM image. Furthermore, homogenous truly amorphous samples are isotropic and do not require much averaging. For most cases, the TEM/nanodiffraction or SAED mode is sufficient and more straightforward for obtaining high quality data for ePDFs.

Electron diffraction data for PDF analysis can also be collected using a non-TEM experimental setup. The idea of a dedicated camera for electron diffraction experiments in transmission mode was very popular in the middle of the last century. Several cameras were built and used for structure analysis of polycrystalline materials. Unfortunately no commercial version of the electron diffraction camera is currently available, but this may change in the near future given recent developments in electron crystallography. Electron diffraction data obtained in reflection geometry does not give information about the bulk, but carries information on the structural features of the near surface region. In principle these kinds of data may also be used for PDF analysis. The PDF analyses using grazing incidence with electrons, also lower energy electrons has already been demonstrated for inorganic gold nanoparticles. Similar investigations should also be possible, for example for organic nanoparticles or amorphous or nanocrystalline organic films.

Computer Analysis

Figure 19:
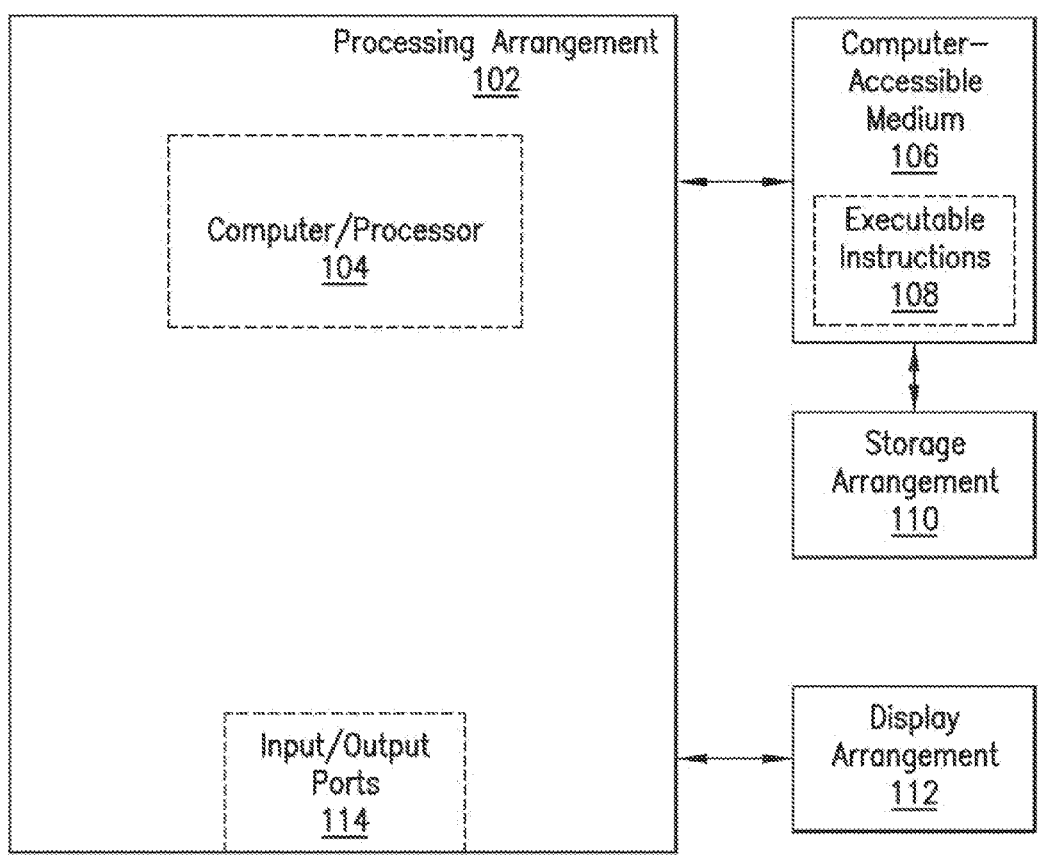
FIG. 19 shows a block diagram of an exemplary computing arrangement capable of implementing the methods described herein.

FIG. 19 shows an exemplary block diagram of an exemplary embodiment of a system according to the present disclosure. For example, exemplary procedures in accordance with the present disclosure described herein can be performed by a processing arrangement and/or a computing arrangement 102. Such processing/computing arrangement 102 can be, e.g., entirely or a part of, or include, but not limited to, a computer/processor 104 that can include, e.g., one or more microprocessors, and use instructions stored on a computer-accessible medium (e.g., RAM, ROM, hard drive, or other storage device).

As shown in FIG. 10, e.g., a computer-accessible medium 106 (e.g., as described herein above, a storage device such as a hard disk, floppy disk, memory stick, CD-ROM, RAM, ROM, etc., or a collection thereof) can be provided (e.g., in communication with the processing arrangement 102). The computer-accessible medium 106 can contain executable instructions 108 thereon. In addition or alternatively, a storage arrangement 110 can be provided separately from the computer-accessible medium 106, which can provide the instructions to the processing arrangement 102 so as to configure the processing arrangement to execute certain exemplary procedures, processes and methods, as described herein above, for example.

Further, the exemplary processing arrangement 102 can be provided with or include an input/output arrangement 114, which can include, e.g., a wired network, a wireless network, the internet, an intranet, a data collection probe, a sensor, etc. As shown in FIG. 10, the exemplary processing arrangement 102 can be in communication with an exemplary display arrangement 112, which, according to certain exemplary embodiments of the present disclosure, can be a touch-screen configured for inputting information to the processing arrangement in addition to outputting information from the processing arrangement, for example. Further, the exemplary display 112 and/or a storage arrangement 110 can be used to display and/or store data in a user-accessible format and/or user-readable format.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. In addition, all publications and references referred to above can be incorporated herein by reference in their entireties. It should be understood that the exemplary procedures described herein can be stored on any computer accessible medium, including a hard drive, RAM, ROM, removable disks, CD-ROM, memory sticks, etc., and executed by a processing arrangement and/or computing arrangement which can be and/or include a hardware processors, microprocessor, mini, macro, mainframe, etc., including a plurality and/or combination thereof. In addition, certain terms used in the present disclosure, including the specification, drawings and claims thereof, can be used synonymously in certain instances, including, but not limited to, e.g., data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it can be explicitly incorporated herein in its entirety.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

What is claimed is:

1. A method for determining an atomic pair distribution function of a sample, comprising:

exposing the sample to an electron beam, wherein the sample scatters electrons from the electron beam;
detecting the scattered electrons with a detector, thereby obtaining a diffraction pattern of the sample;
manipulating at least one of the sample or the electron beam to limit exposure of at least a portion of the sample to the electron beam; and
analyzing the diffraction pattern to determine the atomic pair distribution function of the sample.

2. The method of claim 1, wherein limiting the exposure of the portion of the sample comprises limiting the exposure to be below a critical electron dose.

3. The method of claim 2, wherein the critical electron dose is a dose that causes less than 37% decay of the Bragg intensities.

4. The method of claim 2, wherein the critical electron dose is a dose that causes less than a 37% change in the height of a peak in the PDF that is not a near-neighbor peak.

5. The method of claim 1, wherein the diffraction pattern is obtained by a low-voltage electron microscope.

6. The method of claim 5, wherein the electron microscope operates at a voltage lower than 80 kV.

7. The method of claim 1, wherein the diffraction pattern is obtained by a transmission electron microscope.

8. The method of claim 1, wherein the diffraction pattern is obtained by a transmission electron microscope that is equipped with an STEM unit.

9. The method of claim 1, wherein a portion of the electron beam passes through the sample.

10. The method of claim 9, wherein the electron beam impacts the center of the detector.

11. The method of claim 9, wherein the electron beam impacts a corner of the detector.

12. The method of claim 9, wherein the electron beam does not impact the detector.

13. The method of claim 1, wherein the diffraction pattern is obtained in transmission geometry.

14. The method of claim 1, wherein the diffraction pattern is obtained in reflection geometry.

15. The method of claim 1, additionally comprising:
recording the location of the central beam relative to the detector;
and wherein the diffraction pattern comprises an electron diffraction image.

16. The method of claim 15, wherein the analyzing step comprises:
azimuthally integrating the electron diffraction image, wherein the integration produces the integrated intensity as a function of an independent variable x; and
correcting the integrated intensity for intensity aberrations in the sample to obtain i(x).

17. The method of claim 1, wherein the sample is an organic material.

18. The method of claim 1, wherein the sample is an organometallic material.

19. The method of claim 1, wherein the sample is a metal-organic complex.

20. A method for determining an atomic pair distribution function and for collecting electron diffraction data from multiple substantially unexposed areas of an organic or organometallic sample, comprising:
(a) illuminating an area of the organic or organometallic sample with an electron beam, wherein the beam has a diameter $D_0$ at an intersection with the sample;
(b) collecting electron diffraction data from the illuminated area of the sample, wherein the data is collected by a detector; and (c) repeating steps (a)-(b) on areas of the sample that have not previously been illuminated.

21. The method of claim 20, wherein the electron beam has a source and a selected area aperture with diameter $D_{SA}$ is present between the source and the sample.

22. A method for determining one or more atomic pair distribution functions associated with a material, comprising:
   (a) identifying one or more regions of an organic or organometallic sample from which a signal is to be obtained;
   (b) exposing the sample to a beam of electrons and obtaining a diffraction pattern of the sample;
   (c) classifying each signal according to a classification scheme;
   (d) determining the number of distinct structural forms that have been detected; and
   (e) determining the PDF associated with each identified structural form.

23. The method of claim 22, wherein the classifying step includes determining whether the diffraction pattern have distinct structural types, and further wherein the structural types are determined by examining an entire set of signals as a whole.

24. A method for determining an atomic pair distribution function of a sample, comprising:
   exposing the sample to a beam of electrons, wherein the sample scatters electrons from the electron beam;
   detecting the scattered electrons with a detector, thereby obtaining a diffraction pattern of the sample;
   determining the atomic pair distribution function of the sample by analyzing the diffraction pattern.

25. A system for generating an atomic pair distribution function (PDF) associated with a sample, comprising:
   a non-transitory computer-accessible medium which include instruction therein, wherein,
   when the instructions are executed by a computing arrangement, the computing arrangement is configured to execute procedures comprising
   obtaining a diffraction pattern from at least one portion of the sample to which electrons have been provided; and
   determining the PDF associated with the sample by analyzing the diffraction pattern, procedure.

* * * * *